United States Patent
Takahashi et al.

(10) Patent No.: US 11,925,114 B2
(45) Date of Patent: Mar. 5, 2024

(54) INDENOCARBAZOLE COMPOUND AND ORGANIC ELECTROLUMINESCENCE DEVICE

(71) Applicant: HODOGAYA CHEMICAL CO., LTD., Tokyo (JP)

(72) Inventors: Takehiro Takahashi, Tokyo (JP); Hideyoshi Kitahara, Tokyo (JP); Junichi Izumida, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 473 days.

(21) Appl. No.: 16/342,410

(22) PCT Filed: Oct. 18, 2017

(86) PCT No.: PCT/JP2017/037746
§ 371 (c)(1),
(2) Date: Apr. 16, 2019

(87) PCT Pub. No.: WO2018/074529
PCT Pub. Date: Apr. 26, 2018

(65) Prior Publication Data
US 2020/0058879 A1 Feb. 20, 2020

(30) Foreign Application Priority Data
Oct. 19, 2016 (JP) .................. 2016-205109

(51) Int. Cl.
*H10K 85/60* (2023.01)
*C07D 209/94* (2006.01)
(Continued)

(52) U.S. Cl.
CPC ....... *H10K 85/6572* (2023.02); *C07D 209/94* (2013.01); *C07D 405/14* (2013.01);
(Continued)

(58) Field of Classification Search
CPC ............. H01L 51/0072; H01L 51/0073; H01L 51/5012; H01L 51/5016; H01L 51/5056;
(Continued)

(56) References Cited

U.S. PATENT DOCUMENTS

2012/0068170 A1 3/2012 Pflumm et al.
2013/0126856 A1* 5/2013 Yokoyama ........... C07D 401/10
257/40

(Continued)

FOREIGN PATENT DOCUMENTS

CN 102448946 A 5/2012
CN 103038215 A 4/2013
(Continued)

OTHER PUBLICATIONS

International Search Report in International Application No. PCT/JP2017/037746, filed Oct. 18, 2017.
(Continued)

*Primary Examiner* — Michael Y Sun
(74) *Attorney, Agent, or Firm* — Saliwanchik, Lloyd & Eisenschenk

(57) ABSTRACT

The present invention provides an indenocarbazole compound characterized by having hole transporting properties, being used as a constituent material of an organic electroluminescence device, and being represented by the following general formula (1), and an organic electroluminescence device having a pair of electrodes and at least one organic layer sandwiched therebetween is characterized in that the indenocarbazole compound is used as a constituent material of at least one organic layer. The indenocarbazole compound according to the present invention has (1) excellent hole transporting properties, (2) excellent electron blocking properties, (3) a stable thin film state, and excellent heat resistance. The organic electroluminescence device according to
(Continued)

the present invention has a high light-emitting efficiency and high brightness.

7 Claims, 10 Drawing Sheets

(51) Int. Cl.
    *C07D 405/14*     (2006.01)
    *C09K 11/06*     (2006.01)
    *H10K 50/11*     (2023.01)
    *H10K 50/15*     (2023.01)
    *H10K 50/17*     (2023.01)
    *H10K 50/18*     (2023.01)
    *H10K 101/10*     (2023.01)

(52) U.S. Cl.
    CPC .......... *C09K 11/06* (2013.01); *H10K 85/6574* (2023.02); *C09K 2211/1025* (2013.01); *H10K 50/11* (2023.02); *H10K 50/15* (2023.02); *H10K 50/17* (2023.02); *H10K 50/18* (2023.02); *H10K 2101/10* (2023.02)

(58) Field of Classification Search
    CPC . H01L 51/5088; H01L 51/5096; H01L 51/50; C07D 209/94; C07D 405/14; C07D 209/86; C09K 11/06; C09K 2211/1025
    See application file for complete search history.

(56) References Cited

U.S. PATENT DOCUMENTS

| | | | |
|---|---|---|---|
| 2013/0240796 A1* | 9/2013 | Parham | H01L 51/0072 252/500 |
| 2014/0014940 A1 | 1/2014 | Pflumm et al. | |
| 2014/0225040 A1* | 8/2014 | Parham | C07D 403/04 544/70 |
| 2014/0275530 A1 | 9/2014 | Jatsch et al. | |
| 2014/0364625 A1* | 12/2014 | Ahn | C07D 405/04 548/418 |
| 2015/0318478 A1 | 11/2015 | Pflumm et al. | |
| 2015/0333274 A1 | 11/2015 | Parham et al. | |
| 2016/0035992 A1 | 2/2016 | Stroessel et al. | |
| 2016/0248023 A1* | 8/2016 | Parham | C07F 15/0086 |
| 2016/0315268 A1 | 10/2016 | Stoessel | |
| 2017/0018722 A1 | 1/2017 | Jatsch et al. | |
| 2017/0033296 A1 | 2/2017 | Parham et al. | |
| 2019/0088878 A1 | 3/2019 | Parham et al. | |
| 2019/0119260 A1 | 4/2019 | Parham et al. | |
| 2022/0119373 A1 | 4/2022 | Parham et al. | |

FOREIGN PATENT DOCUMENTS

| | | |
|---|---|---|
| CN | 103477462 A | 12/2013 |
| CN | 103889952 A | 6/2014 |
| CN | 104039921 A | 9/2014 |
| CN | 104837808 A | 8/2015 |
| CN | 105074950 A | 11/2015 |
| CN | 105103328 A | 11/2015 |
| CN | 105636959 A | 6/2016 |
| CN | 106467484 A | 3/2017 |
| CN | 106467524 A | 3/2017 |
| JP | 2004-241374 A | 8/2004 |
| JP | 2006-24830 A | 1/2006 |
| JP | 2012-528088 A | 11/2012 |
| JP | 2014-513418 A | 5/2014 |
| JP | 2015-501304 A | 1/2015 |
| JP | 2016-520999 A | 7/2016 |
| JP | 2019-510011 A | 4/2019 |
| JP | 2019-512476 A | 5/2019 |
| KR | 10-2010-0130197 A | 12/2010 |
| KR | 10-2013-0093106 A | 8/2013 |
| KR | 10-2014-0081879 A | 7/2014 |
| KR | 10-2015-0140356 A | 12/2015 |
| KR | 20160020159 A * | 2/2016 |
| WO | WO-2010/136109 A1 | 12/2010 |
| WO | WO-2011/070963 A1 | 6/2011 |
| WO | WO-2012/014500 A1 | 2/2012 |
| WO | WO-2012/117973 A1 | 9/2012 |
| WO | WO-2013/073896 A1 | 5/2013 |
| WO | 2013/157886 A1 | 10/2013 |
| WO | WO-2014/009310 A1 | 1/2014 |
| WO | WO-2014/090368 A1 | 6/2014 |
| WO | WO-2014/166584 A1 | 10/2014 |
| WO | WO-2014/204464 A1 | 12/2014 |
| WO | WO-2015/051869 A1 | 4/2015 |
| WO | 2015/154843 A1 | 10/2015 |
| WO | WO-2016/119992 A1 | 8/2016 |
| WO | WO-2016/186321 A1 | 11/2016 |
| WO | 2017/148564 A1 | 9/2017 |
| WO | 2017/148565 A1 | 9/2017 |

OTHER PUBLICATIONS

Office Action dated Dec. 28, 2020 in Chinese Application No. 201780064324.3.
Office Action dated Jan. 15, 2021 in Japanese Application No. 2018-546390.
Endo, A. et al., "Efficient up-conversion of triplet excitons into a singlet state and its application for organic light emitting diodes," *Applied Physics Letters*, 2011, 98:1-3, American Institute of Physics.
Lee, S. Y. et al., "High-efficiency organic light-emitting diodes utilizing thermally activated delayed fluorescence from triazine-based donor-acceptor hybrid molecules," *Applied Physics Letters*, 2012, 101:1-4, American Institute of Physics.
Tanaka, H. et al., "Efficient green thermally activated delayed fluorescence (TADF) from a phenoxazine-triphenyltriazine (PXZ-TRZ) derivative†," *Chemical Communications*, Dec. 4, 2012, 48(93):11369-11468, The Royal Society of Chemistry.
Uoyama, H. et al., "Highly efficient organic light-emitting diodes from delayed fluorescence," *Nature*, Dec. 13, 2012, 492:234-240, Macmillan Publishers Limited.
European Search Report dated Apr. 3, 2020 in European Application No. 17861864.1.
Office Action dated Nov. 17, 2021 in Chinese Application No. 201780064324.3.
Office Action dated Nov. 16, 2021 in European Application No. 17 861 864.1.
Office Action dated Feb. 21, 2022 in Korean Application No. 10-2019-7013756.
Office Action dated Aug. 15, 2022 in Japanese Application No. 2021-137690.
Office Action dated Aug. 1, 2022 in Korean Application No. 10-2019-7013756.
Office Action dated Sep. 25, 2023 in European Application No. 17 861 864.1.
Office Action dated Jun. 30, 2021 in Chinese Application No. 201780064324.3, along with its English translation.
Office Action dated May 25, 2021 in Japanese Application No. 2018-546390, along with its English translation.

* cited by examiner (Compound 17)

(Compound 18)

(Compound 19)

(Compound 20)

(Compound 21)

(Compound 22)

(Compound 23)

(Compound 24)

INDENOCARBAZOLE COMPOUND AND ORGANIC ELECTROLUMINESCENCE DEVICE

CROSS-REFERENCE TO RELATED APPLICATIONS

This application is the U.S. national stage application of International Patent Application No. PCT/JP2017/037746, filed Oct. 18, 2017; which claims the benefit under 35 U.S.C. § 119 of Japanese Application No. 2016-205109, filed Oct. 19, 2016; the disclosures of each of which are incorporated herein by reference in their entirety.

TECHNICAL FIELD

The present invention relates to a compound suitable for an organic electroluminescence device (hereinafter, referred to as "organic EL device") that is suitable for various display apparatuses and the organic EL device and more particularly to a specific indenocarbazole compound and an organic EL device using the compound.

BACKGROUND ART

An organic EL device is a self-light-emitting device, is brighter than a liquid crystal device, is excellent in visibility, and is capable of clearly displaying. For that reason, active studies have been made.

In recent years, as an attempt to enhance a light-emitting efficiency of an device, an device that generates phosphorescence using a phosphorescence-emitting substance, i.e., uses light emission from a triplet excited state has been developed. According to the excitation state theory, in a case where phosphorescence emission is used, remarkable improvement in the emitting efficiency can be expected, i.e., about 4 times the light-emitting efficiency of fluorescent emission in the related art becomes possible. In 1993, M. A. Baldo et al. in Princeton University realized an external quantum efficiency of 8% by the use of a phosphorescence-emitting device using an iridium complex.

In the organic EL device, a carrier is injected into a light-emitting material from both positive and negative electrodes, to thereby generating the light-emitting material in an excited state and emitting light. In general, in a case of the organic EL device in a carrier injecting type, it is said that excitons excited to an excited singlet state are 25% of the excitons generated and the excitons excited to an excited triplet state are the rest, i.e., 75% of excitons generated. Accordingly, it appears that an energy utilization efficiency is higher when phosphorescence that emits light from the excited triplet state is used. However, since the phosphorescence has a long lifetime in the excited triplet state, deactivation of energy occurs by saturation of the excited state and interaction with excitons in the excited triplet state. Thus, in many cases, a phosphorescence quantum yield of the phosphorescence-emitting substance is generally not high.

In order to solve such a problem, it is conceivable to utilize a delayed fluorescent material showing delayed fluorescence. A certain fluorescent material emits fluorescence, after energy transition to the excited triplet state occurs by an intersystem crossing or the like, by triplet-triplet annihilation or by absorption of thermal energy through an inverse intersystem crossing to the excited singlet state. In the organic EL device, the latter, i.e., a thermally activated delayed fluorescent material is believed to be particularly useful.

In fact, in recent years, devices utilizing emission of light by thermally activated delayed fluorescence (TADF) have also been developed. In 2011, Adachi et al., Kyushu University, realized 5.3% of external quantum efficiency using a thermally activated delayed fluorescent material.

In a case where the thermally activated delayed fluorescent material is used in the organic EL device, the excitons in the excited singlet state emit normal fluorescence (immediate fluorescence). On the other hand, the excitons in the excited triplet state absorb heat generated from an device and emit delayed fluorescence through the inverse intersystem crossing to the excited singlet state. The delayed fluorescence is emitted from the excited singlet state, has the same wavelength as the immediate fluorescence, is generated through the inverse intersystem crossing from the excited triplet state to the excited singlet state, and has thus a longer light emission lifetime than the immediate fluorescence or the phosphorescence. Therefore, it is observed as fluorescence delayed slower than the immediate fluorescence or the phosphorescence. By using such a thermally activated exciton moving mechanism, i.e., by absorbing heat energy after the carrier injection, it is possible to increase a percentage of the excitons in the excited singlet state exceeding 25%. Generally, the percentage of the excitons is only 25%. For example, if a compound that emits strong fluorescence and the delayed fluorescence is used even at a low temperature of lower than 100° C., the inverse intersystem crossing from the excited triplet state to the excited singlet state sufficiently occurs by heat from the device, and the delayed fluorescence is emitted. This significantly improves the light-emitting efficiency of the organic EL device (Patent Literatures 1 and 2).

In the organic EL device, charges injected from both electrodes are recombined in a light-emitting layer and light is emitted. Therefore, in the organic EL device, it is important to how efficiently deliver both charges of holes and electrons to the light-emitting layer. A high light-emitting efficiency can be provided by improving a probability of recombining holes and electrons by improving hole injecting properties into the light-emitting layer, improving electron blocking properties that block electrons injected from a cathode at an anode side of the light-emitting layer; and further by confining the excitons generated in the light-emitting layer. Accordingly, a hole transporting material having hole transporting properties that is used for forming a hole injecting layer, a hole transporting layer, an electron blocking layer, or the light-emitting layer plays an important role. The hole transporting material is required to have a great hole mobility, high hole injecting properties, great electron blocking properties, high triplet energy, and high durability to electrons.

Also, heat resistance and amorphousness of the material are important with respect to an device lifetime. The material having low heat resistance is thermally decomposed by heat generated at the time of driving the device even at a low temperature and is deteriorated. Further, in the material having low amorphousness, a thin film thereof is crystallized even in a short time, and the device is undesirably deteriorated. Accordingly, the materials used is required to have properties of high heat resistance and good amorphousness.

As the hole transporting material of the organic EL device heretofore, N,N'-diphenyl-N,N'-di (α-naphthyl)benzidine (NPD) and various aromatic amine derivatives have been known (Patent Literature 1 and Patent Literature 2). The NPD shows good hole transporting properties, but a low glass transition point (Tg) of as low as 96° C. that is a heat-resistant indicator. Under a high temperature condition, device properties are lowered due to crystallization. Further, some of aromatic amine derivatives described in Patent Literature 1 and Patent Literature 2 have excellent hole mobility of greater than $10^{-3}$ cm$^2$/Vs or more but have insufficient electron blocking properties. Therefore, in the organic EL device formed by using such aromatic amine derivatives, a part of electrons passes through the light-emitting layer and an improvement of the light-emitting efficiency is not be expected. Accordingly, for higher efficiency, it is desirable to provide a material having higher electron blocking properties, forming a more stable thin film, and having high heat resistance.

As the compound having improved properties such as the heat resistance, the hole injecting properties, the hole transporting properties, and the electron blocking properties, an aromatic tertiary amine compound A represented by the following formula has been proposed (Patent Literature 3).

zole derivative represented by the following formula (Y) has been proposed (Patent Document 4).

[Chemical formula 2]

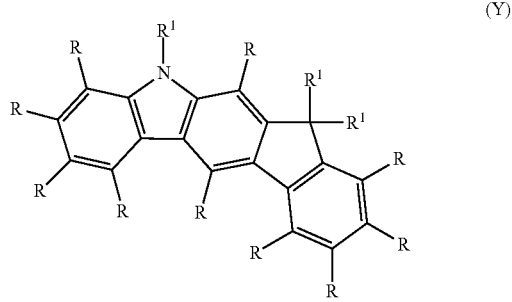

(Y)

However, according to Patent Document 4, in the organic EL device using the compound in the electron blocking layer, a slight improvement was only seen in power efficiency. Moreover, there is no description about the organic EL device using the compound and using the thermally activated delayed fluorescent material as a dopant material of the light-emitting layer.

Thus, in order to improve the device properties of the organic EL device, it is desirable to provide a material being excellent in the hole transporting properties, the hole injecting properties, the electron blocking properties, stability of

[Chemical formula 1]

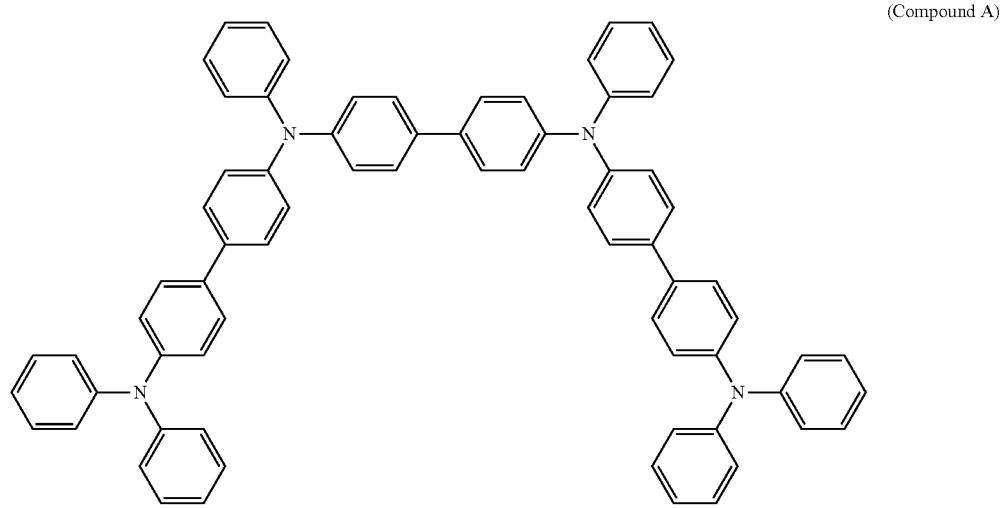

(Compound A)

However, in the device using the compound A as the hole injecting layer, the hole transporting layer, or the electron blocking layer, the heat resistance and the light-emitting efficiency are improved, but are not yet sufficient. Further, there is room for improvement in a driving voltage and a current efficiency, and the amorphousness is also poor. Further, Patent Literature 3 does not describe nor suggest the use of the delayed fluorescent material as the light-emitting material in the organic EL device using the compound.

Further, as a compound having electron transporting properties and hole transporting properties, an indenocarbaa thin film state, and the like that can be used as the hole transporting material in the organic EL device.

CITATION LIST

Patent Literature

Patent Literature 1: Japanese Patent Application Laid-open No. 2004-241374
Patent Literature 2: Japanese Patent Application Laid-open No. 2006-024830

Patent Literature 3: WO2012/117973
Patent Literature 4: WO2010/136109

Non-Patent Literature

Non-Patent Literature 1: Appl. Phys. Let., 98, 083302 (2011)
Non-Patent Literature 2: Appl. Phys. Let., 101, 093306 (2012)
Non-Patent Literature 3: Chem. Commun., 48, 11392 (2012)
Non-Patent Literature 4: NATURE 492, 235 (2012)

DISCLOSURE OF INVENTION

Technical Problem

An object of the present invention is to provide an indenocarbazole compound having (1) excellent hole transporting properties, (2) excellent electron blocking properties, (3) a stable thin film state, and excellent heat resistance as a material having hole transporting properties and suitably used for formation of an organic EL device, in particular, as a material suitably used for a hole transporting layer, a hole injecting layer, or an electron blocking layer in a case where a delayed fluorescent material is used as the dopant material in a light-emitting layer.

Another object of the present invention is to provide an organic EL device having a high light-emitting efficiency and high brightness.

In order to achieve the above-described objects, the present inventors have focused on the fact that an indenocarbazole derivative having a specific structure has the hole transporting properties, is excellent in the thin film stability and durability, and has high energy level in the lowest triplet state ($T_1$). Accordingly, the present inventors have designed and synthesized various indenocarbazole compounds and have intensively evaluated physical properties. As a result, it has discovered that an indenocarbazole compound has the excellent hole transporting properties, the excellent electron blocking properties, a stable thin film state, and excellent heat resistance, the indenocarbazole compound substituted with an aromatic hydrocarbon group, an aromatic heterocyclic group, or a disubstituted amino group substituted with the aromatic hydrocarbon group or the aromatic heterocyclic group, at a specific position.

Furthermore, the present inventors have produced various organic EL devices by using the indenocarbazole compound and have intensively evaluated properties of the devices. As a result, the present invention has been accomplished.

Specifically, the present invention provides an indenocarbazole compound characterized by having hole transporting properties, being used as a constituent material of an organic electroluminescence device, and being represented by the following general formula (1).

[Chemical formula 3]

(1)

wherein
$R^1$ to $R^{12}$ may be the same or different and each represents a hydrogen atom; a deuterium atom; a fluorine atom; a chlorine atom; a cyano group; a nitro group; an alkyl group having 1 to 8 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; an aryloxy group; or a disubstituted amino group substituted with an aromatic hydrocarbon group or an aromatic heterocyclic group, $R^1$ to $R^{12}$ may bond to form a ring via a single bond, a substituted or unsubstituted methylene group, an oxygen atom or a sulfur atom, and X represents an aromatic hydrocarbon group; an aromatic hydrocarbon group; or a disubstituted amino group substituted with an aromatic heterocyclic group or aromatic heterocyclic group.

A preferred embodiment of the indenocarbazole compound according to the present invention is as follows.
1) the indenocarbazole compound according to the present invention represented by the following general formula (1-1).

[Chemical formula 4]

(1-1)

wherein
$R^1$ to $R^{12}$ and X are the meaning described in the general formula (1).
2) the alkyl group having 1 to 8 carbon atoms represented by $R^1$ to $R^{12}$ is an alkyl group having 1 to 6 carbon atoms.
3) X is an aromatic heterocyclic group or a disubstituted amino group.
4) X is a nitrogen-containing aromatic heterocyclic group.

In the present specification, unless otherwise stated, an alkyl group having 1 to 8 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, and aryloxy group represented by $R^1$ to $R^{12}$ and X may have a substituent, or may be unsubstituted. Further, an aromatic hydrocarbon group or an aromatic heterocyclic group included in the disubstituted amino group as the substituent represented by $R^1$ to $R^{12}$ and X may have further a substituent, or may be unsubstituted.

An aliphatic hydrocarbon group such as an alkyl group, an alkenyl group, and an alkyloxy group, unless otherwise specified, may be linear or branched. An aromatic hydrocarbon group and an aromatic heterocyclic group may have, unless otherwise specified, a single ring structure or a polycyclic structure, or further a condensed polycyclic structure.

Further, according to the present invention, the organic electroluminescence device having a pair of electrodes and at least one organic layer sandwiched therebetween is characterized in that the indenocarbazole compound is used as a constituent material of at least one organic layer.

In the organic electroluminescence according to the present invention, 5) the organic layer is preferably a hole transporting layer, an electron blocking layer, a hole injecting layer, or a light-emitting layer, and
6) the delayed fluorescence is preferably emitted.

Furthermore, according to the present invention, an organic electroluminescence device selectively having a light-emitting layer between a pair of electrodes is characterized in that the indenocarbazole compound is used as a constituent material of the light-emitting layer. The organic electroluminescence in this embodiment preferably emits the delayed fluorescence.

Further, according to the present invention, an organic electroluminescence device having a light-emitting layer and other layer between a pair of electrodes is characterized in that the other layer is a hole injecting layer, a hole transporting layer, or an electron blocking layer, and the indenocarbazole compound is used as a constituent material of the light-emitting layer or the other layer. The organic electroluminescence in this embodiment preferably emits the delayed fluorescence.

Advantageous Effects of Invention

The indenocarbazole compound according to the present invention has a high energy level of the lowest triplet state ($T_1$) and a wide band gap between the HOMO-LUMO. Therefore, it has hole transporting properties, and has one or more of the following properties.

(1) higher hole mobility and higher hole transporting properties than the conventional materials,
(2) high hole-injecting properties,
(3) high electron blocking properties, and
(4) high stability to electrons.

Further, the thin-film state is stable and it is excellent in heat resistance. Because of such properties, the indenocarbazole compound according to the present invention is suitable as a material of the organic EL device. It is also possible to use as a material of an organic photoluminescence device.

Further, the organic EL device according to the present invention using the indenocarbazole compound has the following properties:

(5) high light-emitting efficiency,
(6) high brightness,
(7) low light emission start voltage,
(8) low practical driving voltage, and
(9) low manufacturing costs.

The indenocarbazole compound according to the present invention is suitably used as the material of the hole injecting layer or the hole transporting layer of the organic EL device. In the organic EL device having the hole injecting layer or the hole transporting layer formed by using the indenocarbazole compound according to the present invention, it is possible to confine the generated excitons in the emitting layer, increase a probability of recombining the holes and the electrons, and to obtain the high light-emitting efficiency. Also, the driving voltage is low and the durability is excellent.

Further, the indenocarbazole compound according to the present invention is also suitably used as a constituent material of the electron blocking layer of the organic EL device. This is because the indenocarbazole compound has the excellent electron blocking properties, the excellent hole transporting properties, and the stability of the thin film state is high. The organic EL device having the electron blocking layer produced by using the indenocarbazole compound according to the present invention has high light emission efficiency, a low driving voltage, excellent current resistance, high maximum light-emitting brightness.

Furthermore, the indenocarbazole compound according to the present invention is also suitably used as a material of the light-emitting layer of the organic EL device. The indenocarbazole compound has the excellent hole transporting properties and the wide band gap. Accordingly, by using the indenocarbazole compound according to the present invention as a host material of the light-emitting layer, causing to support a fluorescent light-emitting substance, a phosphorescence-emitting substance or a delayed fluorescent material which is called as a dopant, and forming the light-emitting layer, the organic EL device having the low driving voltage and the improved light-emitting efficiency is achievable.

As described above, by using the indenocarbazole derivative according to the present invention, the organic EL device having improved various properties can be provided. Furthermore, by using the delayed fluorescence material in the light-emitting layer of the organic EL device according to the present invention as the dopant material, it is possible to avoid the use of the light-emitting material containing a rare metal such as iridium and platinum. In other words, expensive and scarce rare metals are not used and the indenocarbazole compound and the delayed fluorescence material are used in combination, the organic EL device according to the present invention advantageous in terms of resources and costs in addition to the above effects is achievable.

MODES FOR CARRYING OUT THE INVENTION

<Indenocarbazole Compound>

Figure 1:
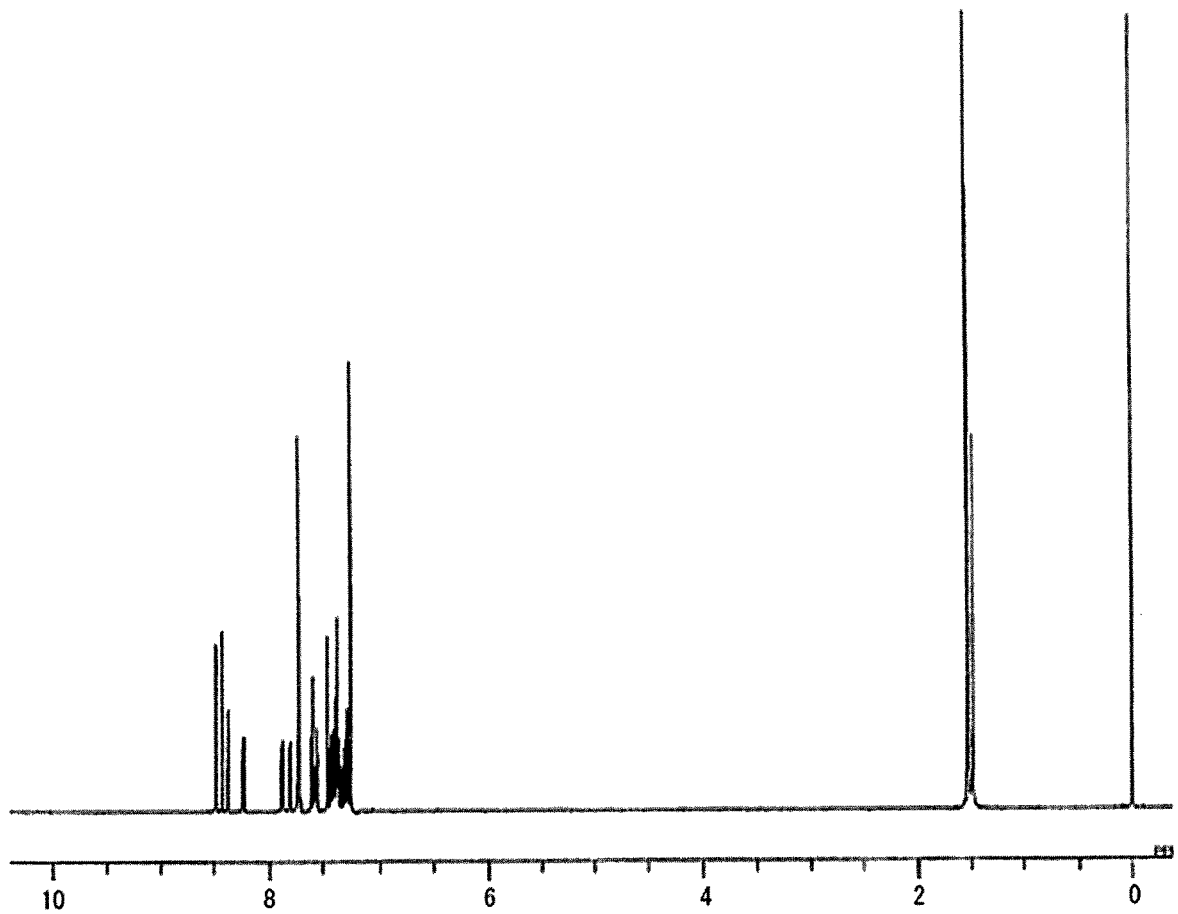
FIG. 1 is a $^1$H-NMR chart diagram of Compound 1 in Example 1.

The indenocarbazole compound according to the present invention is represented by the following general formula (1).

[Chemical formula 5]

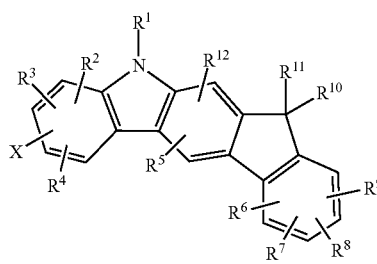

(1)

The indenocarbazole compound represented by the general formula (1) includes an embodiment represented by the following general formula (1-1). This embodiment is the general formula (1) wherein binding positions of X, $R^2$ to $R^9$, and $R^{12}$ are specified.

[Chemical formula 6]

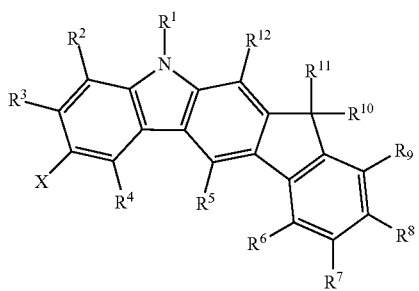

(1-1)

($R^1$ to $R^{12}$)

$R^1$ to $R^{12}$ may be the same or different and each represent a hydrogen atom; a deuterium atom; a fluorine atom; a chlorine atom; a cyano group; a nitro group; an alkyl group having 1 to 8 carbon atoms; a cycloalkyl group having 5 to 10 carbon atoms; an alkenyl group having 2 to 6 carbon atoms; an alkyloxy group having 1 to 6 carbon atoms; a cycloalkyloxy group having 5 to 10 carbon atoms; an aromatic hydrocarbon group; an aromatic heterocyclic group; an aryloxy group; or a disubstituted amino group substituted by a group selected from an aromatic hydrocarbon group or an aromatic heterocyclic group.

$R^1$ to $R^{12}$ may be independently present and not to form a ring, but may bond each other via a single bond, a substituted or unsubstituted methylene group, an oxygen atom or a sulfur atom to form a ring. Note that in a case where $R^1$ to $R^{12}$ each is a disubstituted amino group, an aromatic hydrocarbon group or an aromatic heterocyclic group in the disubstituted amino group contributes to a ring formation.

Specific examples of the alkyl group having 1 to 8 carbon atoms, the cycloalkyl group having 5 to 10 carbon atoms or the alkenyl group having 2 to 6 carbon atoms represented by $R^1$ to $R^{12}$ include a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-octyl group; a cyclopentyl group, a cyclohexyl group, a 1-adamantyl group, a 2-adamantyl group, etc.; a vinyl group, an allyl group, a isopropenyl group, a 2-butenyl group; etc. Examples of the alkyl group having 1 to 8 carbon atoms preferably include an alkyl group having 1 to 6 carbon atoms.

The alkyl group having 1 to 8 carbon atoms, the cycloalkyl group having 5 to 10 carbon atoms or the alkenyl group having 2 to 6 carbon atoms represented by $R^1$ to $R^{12}$ may be unsubstituted however it is also suitable to have a substituent. Examples of the substituent include the following groups in addition to a deuterium atom, a cyano group, and a nitro group:

a halogen atom such as a fluorine atom, a chlorine atom, a bromine atom, and an iodine atom; an alkyloxy group having 1 to 6 carbon atoms such as a methyloxy group, an ethyloxy group, and a propyloxy group; an aryloxy group such as a phenyloxy group, a tolyloxy group; an arylalkyloxy group such as a benzyloxy group and a phenethyloxy group; an aromatic hydrocarbon group such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group;

an aromatic heterocyclic group such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group. Note that these substituents may be unsubstituted however they also may be substituted with the above-described exemplified substituents. Further, these substituents may be independently present and not form a ring however they also may bond each other via a single bond, a substituted or unsubstituted methylene group, an oxygen atom or a sulfur atom to form a ring.

Specific examples of the alkyloxy group having 1 to 6 carbon atoms or the cycloalkyloxy group having 5 to 10 carbon atoms represented by $R^1$ to $R^{12}$ include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, a 2-adamantyloxy group.

The alkyloxy group having 1 to 6 carbon atoms or the cycloalkyloxy group having 5 to 10 carbon atoms represented by $R^1$ to $R^{12}$ may be unsubstituted however it may also have a substituent. Examples of the substituent include the same as those described with respect to the alkyl group having 1 to 8 carbon atoms, the cycloalkyl group having 5 to 10 carbon atoms, or the alkenyl group having 2 to 6 carbon atoms represented by $R^1$ to $R^{12}$. The modes that can be taken are also the same.

Specific examples of the aromatic hydrocarbon group or the aromatic heterocyclic group represented by $R^1$ to $R^{12}$ include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, an indenocarbazolyl group, a benzoxazolyl group, a benzothiazolyl group, a quinoxalinyl group, a benzimidazolyl group, a pyrazolyl group, a dibenzodiazepinyl group, a dibenzofuranyl group, a dibenzothienyl group, a naphthyridinyl group, a phenanthrolinyl group, a phenadinyl group, a phenoxazinyl group, a phenoserenadinyl group, a phenothiazinyl group, a phenotellurazinyl group, a phenophosphinadinyl group, an acridinyl group, and a carbolinyl group.

The aromatic hydrocarbon group or the aromatic heterocyclic group represented by $R^1$ to $R^{12}$ may be unsubstituted or may have a substituent. Examples of the substituent include the following groups in addition to a deuterium atom, a cyano group, and a nitro group:

a halogen atom such as fluorine atom, a chlorine atom, a bromine atom, and an iodine atom;

an alkyl group having 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

an alkyloxy group having 1 to 6 carbon atoms such as a methyloxy group, an ethyloxy group, and a propyloxy group;

an alkenyl group having 2 to 6 carbon atoms such as a vinyl group and an allyl group;

an aryloxy group such as a phenyloxy group and a tolyloxy group;

an arylalkyloxy group such as a benzyloxy group, a phenethyloxy group;

an aromatic hydrocarbon group such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group;

an aromatic heterocyclic group such as a pyridyl group, a pyrimidinyl group, a triazinyl group, a furyl group, a thienyl group, a pyrrolyl group, a quinolyl group, an isoquinolyl group, a benzofuranyl group, a benzothienyl group, an indolyl group, a carbazolyl group, an indenocarbazolyl group, a benzoxazolyl group, a benzothiazolyl group, a quinoxalinyl group, a benzimidazolyl group, a pyrazolyl group, a dibenzofuranyl group, a dibenzothienyl group, a carbolinyl group, a phenoxazinyl group, a phenothiazinyl group, an acridinyl group, a phenazinyl group;

an aryl vinyl group such as a styryl group and naphthyl vinyl group;

an acyl groups such as an acetyl group and a benzoyl group; and a disubstituted amino group, such as a dialkylamino group substituted with an alkyl group such as a dimethylamino group and a diethylamino group, a disubstituted amino group substituted with only an aromatic hydrocarbon group such as a diphenylamino group and a dinaphthylamino group, a diaralkylamino group substituted with an aralkyl group such as a dibenzylamino group and a diphenethyl amino group, a disubstituted amino group substituted with only an aromatic heterocyclic group such as a dipyridyl amino group and a dithienylamino group, a dialkenylamino group substituted with an alkenyl group such as diallylamino group, and a disubstituted amino group substituted with a substituent selected from the group consisting of other alkyl group, an aromatic hydrocarbon group, an aralkyl group, an aromatic heterocyclic group, and an alkenyl group.

Note that these substituents may be unsubstituted, however may also be substituted with the above-described exemplified substituents. Further, these substituents may be independently present and not form a ring however may also bond each other via a single bond, a substituted or unsubstituted methylene group, an oxygen atom or a sulfur atom to form a ring. In a case where the substituent is the disubstituted amino group, an alkyl group, an aromatic hydrocarbon group, an aralkyl group, an aromatic heterocyclic group or an alkenyl group constituting the disubstituted amino group contributes to a ring formation.

Specific examples of the aryloxy group represented by $R^1$ to $R^{12}$ include a phenyloxy group, biphenylyloxy group, a terphenyloxy group, a naphthyloxy group, an anthracenyloxy group, a phenanthrenyloxy group, a fluorenyloxy group, an indenyloxy group, a triphenylenyloxy group, a pyrenyloxy group, and a perylenyloxy group.

The aromatic hydrocarbon group or the aromatic heterocyclic group represented by $R^1$ to $R^{12}$ may be unsubstituted however may also have a substituent. Examples of the substituent include the same as those described with respect to the aromatic hydrocarbon group or the aromatic heterocyclic group represented by $R^1$ to $R^{12}$. The embodiments that can be taken are also the same.

Examples of the aromatic hydrocarbon group or the aromatic heterocyclic group of the substituent included in the disubstituted amino group represented by $R^1$ to $R^{12}$ include the same as those described with respect to the aromatic hydrocarbon group or the aromatic heterocyclic group represented by $R^1$ to $R^{12}$.

The aromatic hydrocarbon group or the aromatic heterocyclic group of the substituent included in the disubstituted amino group represented by $R^1$ to $R^{12}$ may be unsubstituted or may further have a substituent. Examples of the substituent group include the same as those described with respect to the substituent that the aromatic hydrocarbon group or the aromatic heterocyclic group represented by $R^1$ to $R^{12}$ may have. The embodiments that can be taken are also the same.

(X)

X represents an aromatic hydrocarbon group, an aromatic heterocyclic group, or a disubstituted amino group substituted by the aromatic hydrocarbon group or the aromatic heterocyclic group.

Examples of the aromatic hydrocarbon group or the aromatic heterocyclic group represented by X may include the same as those described with respect to $R^1$ to $R^{12}$.

The aromatic hydrocarbon group or the aromatic heterocyclic group represented by X may be unsubstituted or may have a substituent. Examples of the substituent include the same as those described with respect to the aromatic hydrocarbon group or the aromatic heterocyclic group represented by $R^1$ to $R^{12}$. The modes that can be taken are also the same.

Examples of the aromatic hydrocarbon group or the aromatic heterocyclic group of the substituent included in the disubstituted amino group represented by X include the same as those described with respect to the aromatic hydrocarbon group or the aromatic heterocyclic group represented by $R^1$ to $R^{12}$.

The aromatic hydrocarbon group or the aromatic heterocyclic group of the substituent included in the disubstituted amino group represented by $R^1$ to $R^{12}$ may be unsubstituted or may further have a substituent. Examples of the substituent include the same as those described with respect to the aromatic hydrocarbon group or the aromatic heterocyclic group represented by $R^1$ to $R^{12}$. The embodiments that can be taken are also the same.

PREFERRED EMBODIMENTS

Hereinafter, preferred embodiments of the indenocarbazole compound will be described.

The indenocarbazole compound is preferably the indenocarbazole compound represented by the general formula (1-1).

$R^1$ is preferably an aromatic hydrocarbon group or an aromatic heterocyclic group and is more preferably an aromatic hydrocarbon group having no condensed polycyclic structure or an aromatic heterocyclic group having a condensed polycyclic structure and having no nitrogen atom as a hetero atom. Also, the above-described aromatic heterocyclic group having no nitrogen atom as a hetero atom is preferably an oxygen-containing aromatic heterocyclic group. Specifically, a phenyl group, a biphenylyl group, a terphenylyl group, a benzofuranyl group, a benzothienyl group, a dibenzofuranyl group, or a dibenzothienyl group are preferable, and a phenyl group, a biphenylyl group or a dibenzofuranyl group are more preferable. The group represented by $R^1$ is preferably unsubstituted.

$R^2$ to $R^9$, and $R^{12}$ each is preferably a hydrogen atom or a deuterium atom, more preferably a hydrogen atom.

$R^{10}$ and $R^{11}$ each is preferably an alkyl group or an aromatic hydrocarbon group having 1 to 8 carbon atoms, more preferably a methyl group, an octyl group or a phenyl group, particularly preferably a methyl group.

X is preferably an aromatic heterocyclic group or a disubstituted amino group, more preferably an aromatic heterocyclic group, particularly preferably a nitrogen-containing aromatic heterocyclic group, most preferably a nitrogen-containing aromatic heterocyclic group having a fused polycyclic structure including 3 or more rings. Specifically, a phenoxazinyl group, a phenothiazinyl group, an acridinyl group, a phenazinyl group, a carbazolyl group, an indenocarbazolyl group, a dibenzofuranyl group, a dibenzothienyl group, a phenanthrolinyl group or a carbolinyl group is preferable, and a dibenzofuranyl group, a carbazolyl group, or an indenocarbazolyl group is more preferable.

Further, in the aromatic heterocyclic group, in view of ease of manufacture, a power efficiency, brightness, etc., an N atom on the aromatic heterocyclic ring is preferably attached to the indenocarbazole skeleton. From the viewpoint of the device lifetime, a nitrogen-containing aromatic heterocyclic group having fused polycyclic structure including 3 or more rings, such as a carbazolyl group and an indenocarbazolyl group is preferable. From the view point of the brightness, a light emission efficiency, and the power efficiency, an aromatic heterocyclic group having a fused polycyclic structure including 3 or more rings and including no nitrogen atom as a hetero atom, e.g., a dibenzothienyl group, or a dibenzofuranyl group are preferable, and a dibenzofuranyl group is more preferable.

Here, a dibenzofuranyl group and a dibenzothienyl group are preferably unsubstituted.

Further, a phenoxazinyl group, phenothiazinyl group, an acridinyl group, a phenazinyl group, a carbazolyl group, an indenocarbazolyl group, a phenanthrolinyl group or a carbolinyl group is unsubstituted or has a substituent. As the substituent, an alkyl group having 1 to 4 carbon atoms; an aromatic hydrocarbon group; an aromatic heterocyclic group; or a disubstituted amino group substituted with an aromatic hydrocarbon group is preferable, a methyl group, a phenyl group, a carbazolyl group, a diphenyl amino group, a biphenylyl group, a fluorenyl group, an indenocarbazolyl group, a dibenzothienyl group or a dibenzofuranyl group is more preferable, a methyl group, a phenyl group, a carbazolyl group, a biphenylyl group, a fluorenyl group, an indenocarbazolyl group, a dibenzothienyl group or a dibenzofuranyl group is particularly preferable, and a methyl group is most preferable.

Specific preferable embodiments of the indenocarbazole compound according to the present invention are shown in FIGS. 6 to 10. However, the indenocarbazole compound is not limited to these compounds. D represents a deuterium atom.

In the specific embodiments, the compounds 1, 4 to 6 and 9 to 23 each has two or more indenocarbazole structures in one molecule. Each indenocarbazole structure drawn in the rightmost on the paper corresponds to a main skeleton of the indenocarbazole compound according to the present invention.

Further, the compounds 1 to 45 in specific embodiments correspond to the above general formula (1-1).

<Manufacturing Method>

The indenocarbazole compound according to the present invention can be produced by known methods. For example, the indenocarbazole compound can be synthesized by performing a condensation reaction such as the Buffubarudo-Hartwig reaction between indenocarbazole that is substituted with halogen such as bromine and amines such as a nitrogen-containing heterocyclic compound in the presence of a base.

More specifically, firstly, by the Buffubarudo-Hartwig reaction between an indenocarbazole derivative and a halide such as halogenated aryl or halogenated heteroaryl in the presence of a palladium catalyst and a base, an indenocarbazole derivative to which a group corresponding to $R^1$ in the general formula (1) is introduced. Next, the resulting indenocarbazole derivative is halogenated by using NBS, etc. Subsequently, by the Buffubarudo-Hartwig reaction between the halogenated indenocarbazole derivative and secondary amine or the Suzuki-Miyaura cross-coupling reaction between the halogenated indenocarbazole derivative and a boronic acid compound such as dibenzofuran boronic acid and dibenzothiophene boronic acid, a group corresponding to X in the general formula (1) is introduced.

The indenocarbazole compound can be purified by column chromatograph purification, adsorption purification with silica gel, activated carbon, activated clay or the like, recrystallization or crystallization with a solvent, or the like. Also, the indenocarbazole compound may be purified by a sublimation purification method. The compound can be identified by an NMR analysis. As physical properties, a glass transition point (Tg), a work function, and the like can be measured.

The glass transition point (Tg) is an index of the stability of the thin film state. The glass transition point (Tg) can be measured by a high sensitive differential scanning calorimeter (manufactured by Bruker AXS, DSC3100S) can be measured by using powder.

The work function is an index of the hole transporting properties. The work function can be determined by preparing a thin film having a thickness of 100 nm on an ITO substrate and by using an ionization potential measuring apparatus (manufactured by Sumitomo Heavy Industries, Ltd., model PYS-202).

The indenocarbazole compound according to the present invention has the hole transporting properties and shows the work function of 5.5 eV or more that is shown by a conventionally known hole transporting material such as NPD, TPD, and the like.

<Organic EL Device>

The above-described indenocarbazole compound according to the present invention is used as a constituent material of the organic EL device. Specifically, in the organic EL device having a structure in which a pair of electrodes and at least one organic layer sandwiched therebetween, the indenocarbazole compound according to the present invention is used for a constituent material of at least one organic layer.

Figure 5:
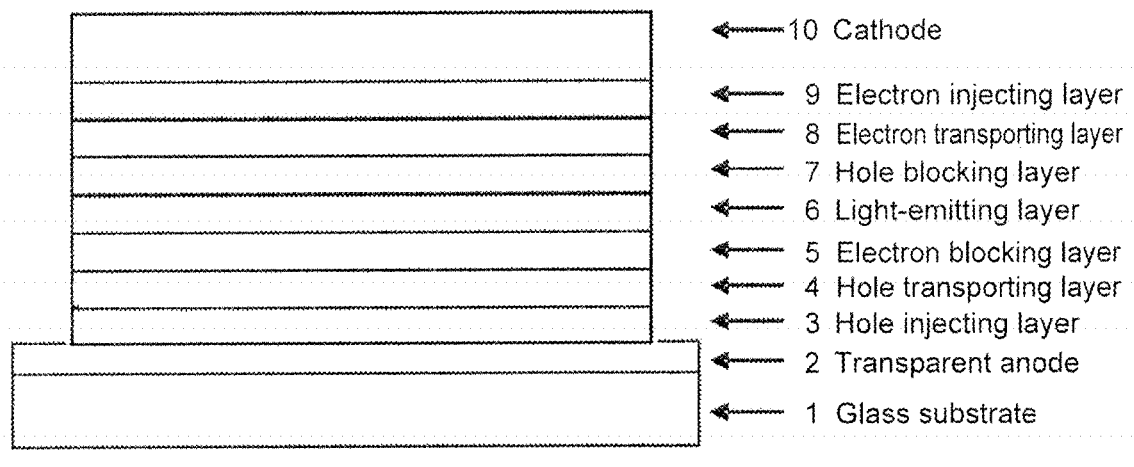
FIG. 5 is a diagram showing a structure of an organic EL device in each of Examples 1 to 4 and Comparative Example 1.
Figure 6:
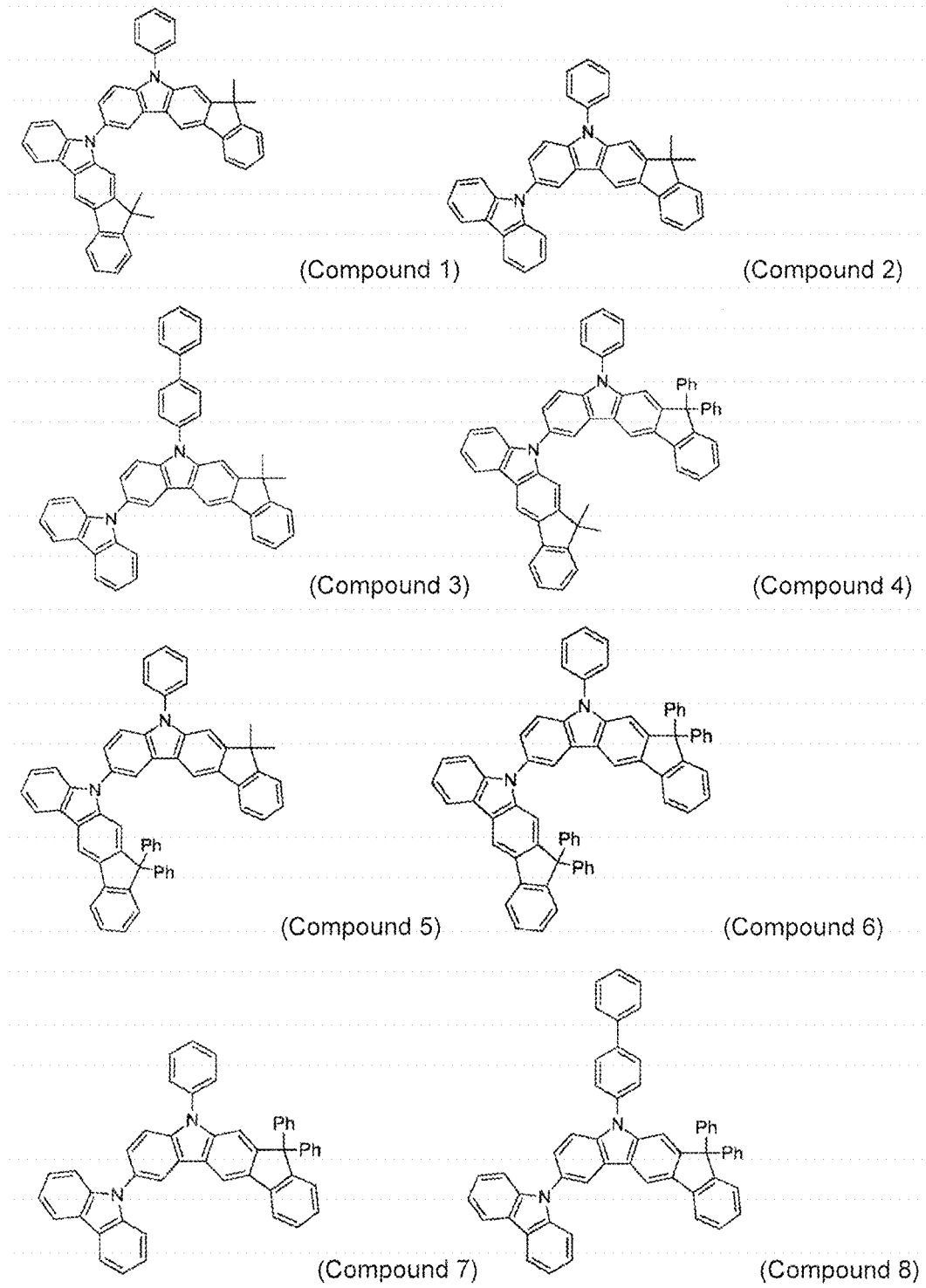
FIG. 6 is a diagram showing structural formulae of Compounds 1 to 8 each of which is an indenocarbazole compound according to the present invention.
Figure 7:
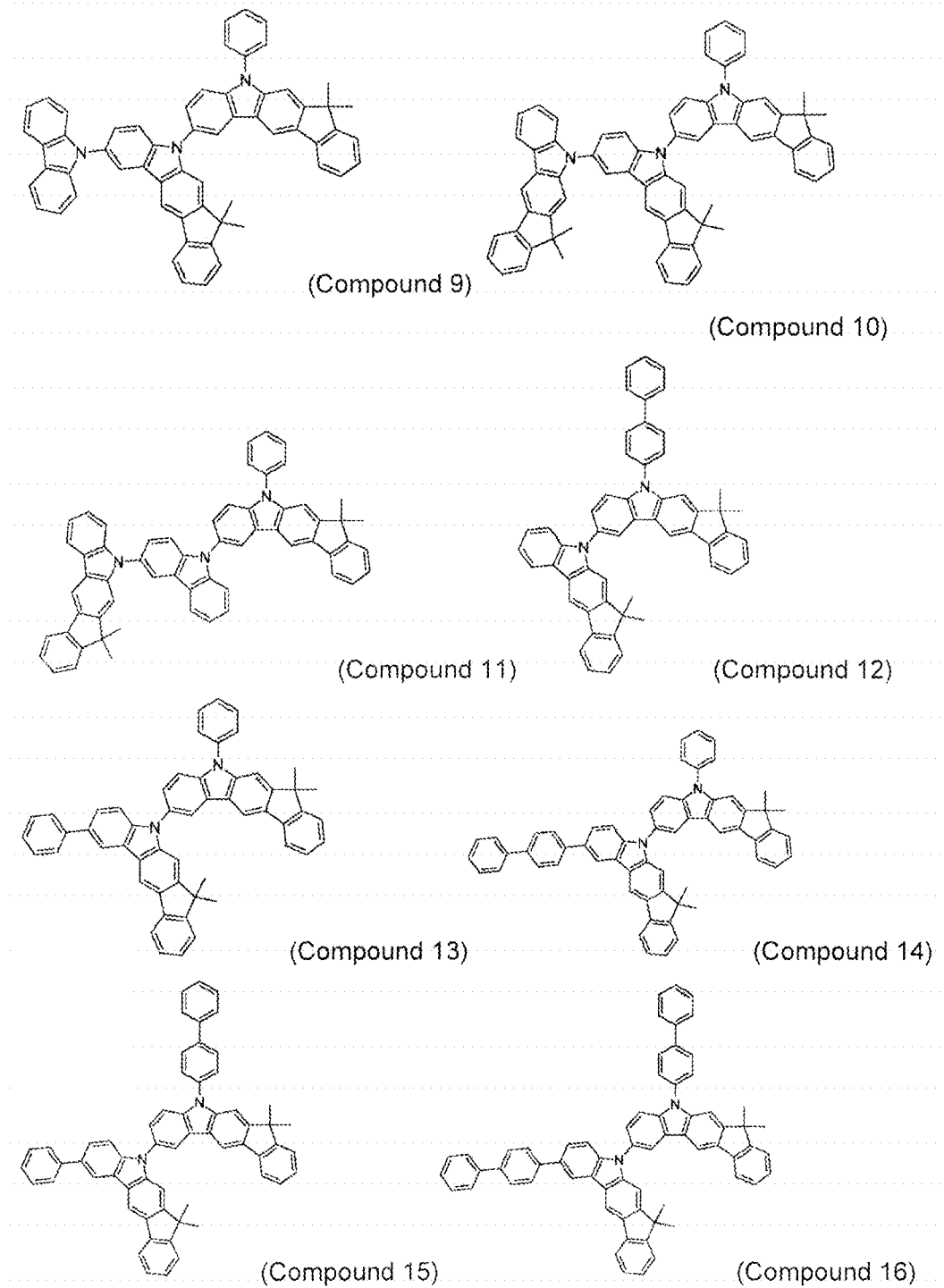
FIG. 7 is a diagram showing structural formulae of Compounds 9 to 16 each of which is the indenocarbazole compound according to the present invention.
Figure 8:
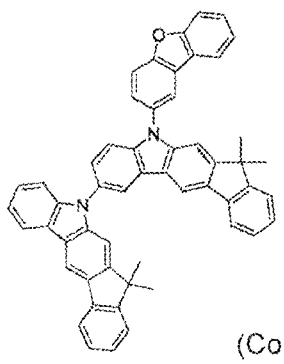
FIG. 8 is a diagram showing structural formulae of Compounds 17 to 24 each of which is the indenocarbazole compound according to the present invention.
Figure 8:
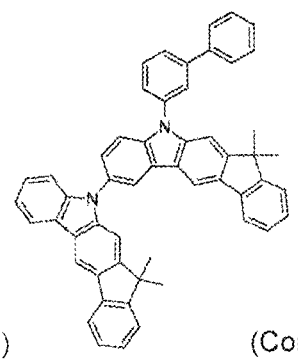
Figure 8:
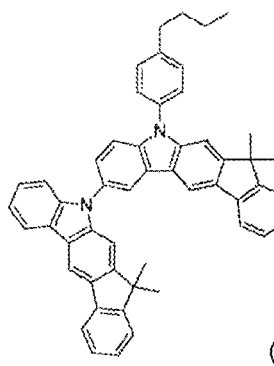
Figure 8:
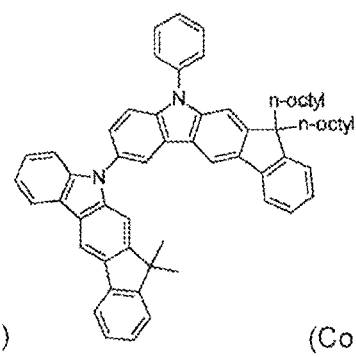
Figure 8:
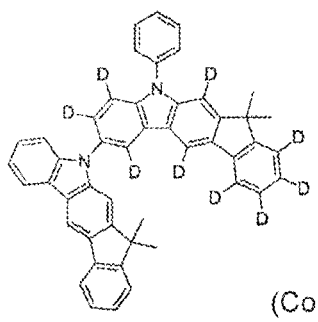
Figure 8:
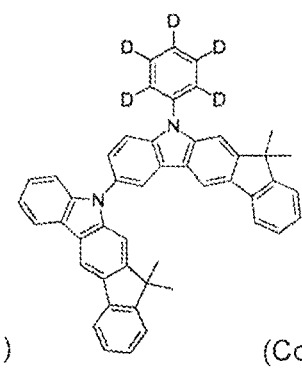
Figure 8:
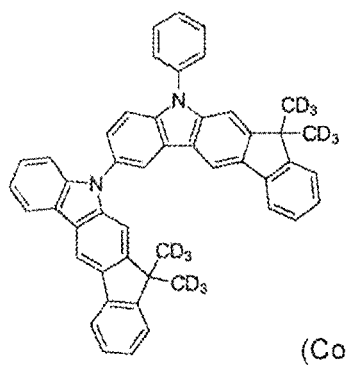
Figure 8:
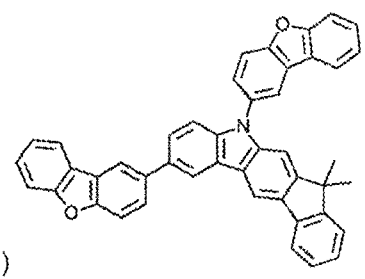
Figure 9:
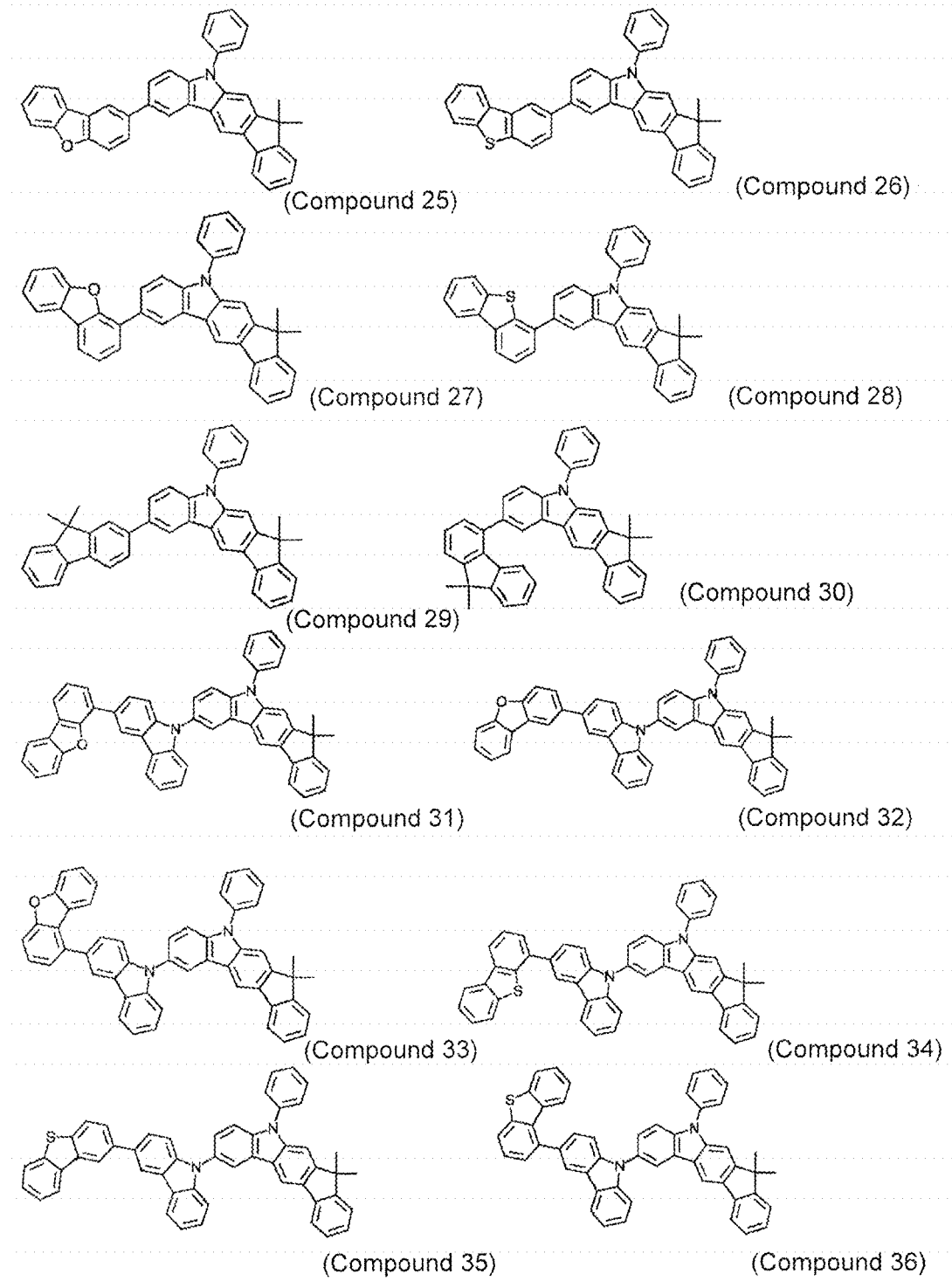
FIG. 9 is a diagram showing structural formulae of Compounds 25 to 36 each of which is the indenocarbazole compound according to the present invention.
Figure 10:
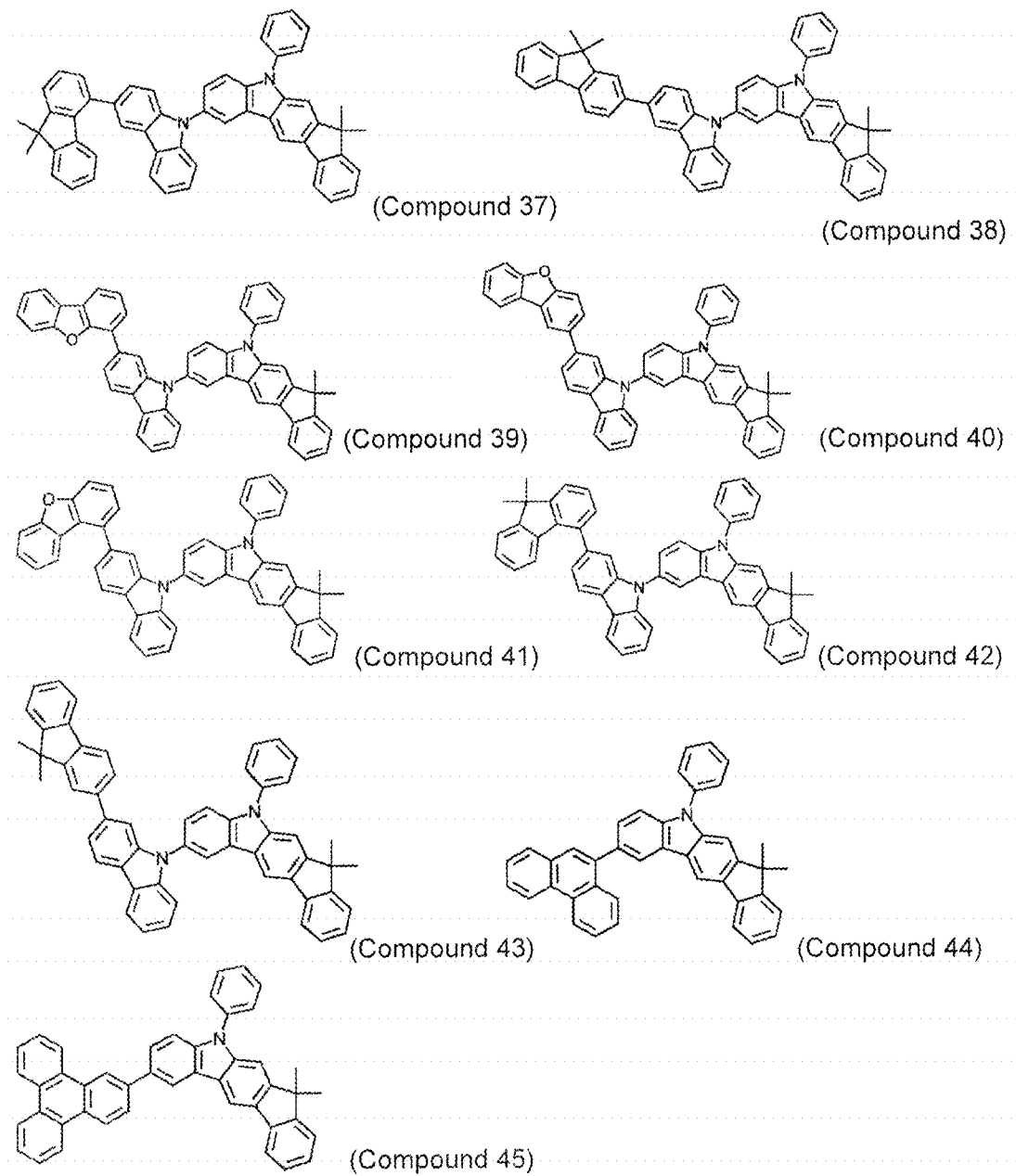
FIG. 10 is a diagram showing structural formulae of Compounds 37 to 45 each of which is the indenocarbazole compound according to the present invention.

As long as the conditions are satisfied, the organic EL device according to the present invention can take various embodiments of layer structures. For example, it is possible to take an embodiment in which only the light-emitting layer is selectively provided between the pair of electrodes. Alternatively, it is possible to take an embodiment in which the light-emitting layer and other layer (hole injecting layer, hole transporting layer, or electron blocking layer) are provided between the pair of electrodes. Specific examples of the embodiment in which the light-emitting layer and other layer are provided include a structure in which an anode, a hole transporting layer, a light-emitting layer, an electron transporting layer, an electron injecting layer, and a cathode are sequentially provided on a substrate. A hole injecting layer may be provided between the anode and the hole transporting layer. An electron blocking layer may be provided between the light-emitting layer and the hole transporting layer. A hole blocking layer may be provided between the light-emitting layer and the electron transporting layer. An exciton blocking layer may be provided on the light-emitting layer at an anode side or a cathode side. Furthermore, it is possible to omit several organic layers or add several functions to one organic layer. For example, it is possible to configure such that the hole injecting layer also functions as the hole transporting layer or the electron transporting layer also functions as the electron injecting layer. Also, it is possible to configure such that two or more organic layers having the same function are laminated. For example, it is possible to configure such that two hole transporting layers are laminated, two light-emitting layers are laminated, two electron transporting layers are laminated, etc. FIG. 5 shows a layer structure employed in the examples described below. Specifically, a layer structure is shown by forming a transparent anode 2, a hole injecting layer 3, a hole transporting layer 4, an electron blocking layer 5, a light-emitting layer 6, a hole blocking layer 7, an electron transporting layer 8, an electron injecting layer 9, and a cathode 10 on a glass substrate 1 in this order.

<Anode>

The anode 2 may be constituted per se by a known electrode material and an electrode material having a large work function such as ITO and gold is used, for example.

<Hole Injecting Layer>

The indenocarbazole compound according to the present invention is suitably used for the hole injecting layer 3. Otherwise, known materials may be used in place of the indenocarbazole compound according to the present invention, or may be used by mixing or simultaneously with the indenocarbazole compound according to the present invention.

Examples of the known materials include a porphyrin compound represented by copper phthalocyanine; a naphthalene diamine derivative; a starburst-type triphenylamine derivative; a triphenylamine trimer or tetramer having a structure that triphenylamines are single-bonded or linked by a divalent group containing no hetero atom; an acceptor-type heterocyclic compound such as hexacyano azatriphenylene; and a coating-type polymer material.

Further, a material to which tris-bromophenyl amine hexa chloro antimony, a radialene derivative (WO 2014/009310), or the like is P-doped, a polymer compound having a partial structure including a structure of a benzidine derivative such as TPD, or the like can be used as well as the materials commonly used for the hole injecting layer.

The hole injecting layer 3 can be provided by forming a thin film by any known method such as a vapor deposition method, a spin coating method, or an inkjet method by using these materials. The respective layers described below can be similarly provided by forming a thin film by any known method such as a vapor deposition method, a spin coating method, or an inkjet method.

<Hole Transporting Layer>

The indenocarbazole compound according to the present invention is suitably used for the hole transporting layer 4. Otherwise, known materials may be used in place of the indenocarbazole compound according to the present invention, or may be used by mixing or simultaneously with the indenocarbazole compound according to the present invention.

Compounds containing m-carbazolylphenyl group;
benzidine derivatives, such as
N,N'-diphenyl-N,N'-di(m-tolyl)-benzidine (TPD),
N,N'-diphenyl-N,N'-di(α-naphthyl)-benzidine (NPD),
N,N,N',N'-tetra-biphenylyl benzidine;
1,1-bis[(di-4-tolylamino)phenyl]cyclohexane (TAPC);
various triphenylamine trimers and tetramers; and
carbazole derivatives.

The hole transporting layer 4 may be formed by using the above-described materials alone, or may be formed by mixing with other materials. The hole transporting layer 4 may have a structure on which layers formed alone are laminated, layers formed by mixing are laminated, or a layer formed alone and a layer formed by mixing are laminated. Other organic layers in addition to the hole transporting layer may also have a similar structure.

Further, the hole injecting layer that also functions as the hole transporting layer can be formed by using the coating-type polymer materials such as poly(3,4-ethylenedioxythiophene) (PEDOT)/poly (styrene sulfonate) (PSS).

Further, a material to which tris-bromophenyl amine hexa chloro antimony, a radialene derivative (WO 2014/009310), or the like is P-doped, a polymer compound having a partial structure including a structure of a benzidine derivative such as TPD, or the like can be used as well as the materials commonly used for the hole transporting layer.

<Electron Blocking Layer>

The indenocarbazole compound according to the present invention is suitably used for the electron blocking layer 5. Otherwise, known compounds having an electron blocking effect may be used exemplified below, for example.

Carbazole derivatives, such as
4,4',4"-tri(N-carbazolyl)triphenylamine (TCTA),
9,9-bis[4-(carbazol-9-yl) phenyl]fluorene,
1,3-bis(carbazol-9-yl) benzene (mCP),
2,2-bis(4-carbazol-9-yl-phenyl)adamantane (Ad-Cz);
triarylamine compound having a triphenylsilyl group, such as,
9-[4-(carbazol-9-yl)phenyl]-9-[4-(triphenylsilyl)phenyl]-9H-fluorene;
a monoamine compound having high electron blocking properties; and
various triphenylamine dimers.

<Light-Emitting Layer>

The indenocarbazole compound according to the present invention may be suitably used for the light-emitting layer 6. Further, known light-emitting materials may be used. Examples of the known light-emitting materials include a delayed fluorescent material including PIC-TRZ (see Non-Patent Literature 1), CC2TA (see Non-Patent Literature 2), PXZ-TRZ (see Non-Patent Literature 3), a carbazolyl dicyanobenzene (CDCB) derivative such 4CzIPN (see non-Patent Literature 4); various metal complexes such as a quinolinol derivative including tris(8-hydroxyquinoline)aluminum ($Alq_3$); a benzonitrile derivative; an anthracene derivative; a bis styryl benzene derivative; a pyrene derivative; an oxazole derivative; a polyparaphenylene vinylene derivative; and the like can be used.

In a case where the organic EL device includes the light-emitting layer formed by using the delayed fluorescent material, the organic EL device emits delayed fluorescence when current flows.

The emitting layer 6 is preferably formed of the host material and the dopant material.

As the host material, in addition to the indenocarbazole compound according to the present invention and the above-described light-emitting material other than the delayed fluorescent material, a benzonitrile derivative, mCP, mCBP, a thiazole derivative, a benzimidazole derivative, a polydialkylfluorene derivative, and the like can be used.

As the dopant material, the delayed fluorescent material including a benzonitrile derivative and a CDCB derivative such as PIC-TRZ, CC2TA, PXZ-TRZ, and 4CzIPN; quinacridone, coumarin, rubrene, anthracene, perylene and derivatives thereof; a benzopyran derivative; a rhodamine derivative; an aminostyryl derivative; and the like can be used.

Further, it is also possible to use a phosphorescence-emitting substance as the light-emitting material. Examples of the phosphorescence-emitting substance include a metal complex of iridium or platinum. Specific examples include a green phosphorescence-emitting substance such as $Ir(ppy)_3$; a blue phosphorescence-emitting substance such as FIrpic and FIr6; and a red phosphorescence-emitting substance such as $Btp_2Ir(acac)$ and $Ir(piq)_3$.

As the host material in this case, it is possible to use the indenocarbazole compound according to the present invention or a heterocyclic compound having an indole ring.

Further, it is possible to use, for example, the following host materials having the hole injecting properties and the hole transporting properties:
Carbazole derivatives such as
4,4'-di(N-carbazolyl)biphenyl (CBP),
TCTA, and
mCP.

Furthermore, it is possible to use, for example, the following host materials having the electron transporting properties:
p-bis(triphenylsilyl) benzene (UGH2), and
2,2',2"-(1,3,5-phenylene)-tris(1-phenyl-1H-benzimidazole) (TPBI).

The use of such a host material can produce a high-performance organic EL device.

Doping to the host material of the phosphorescence-emitting substance is preferably performed by co-vapor deposition in the range of 1 to 30% by weight with respect to the entire light-emitting layer in order to avoid concentration quenching.

The light-emitting layer is preferably formed by using the indenocarbazole compound according to the present invention or the delayed fluorescent material, and is more preferably formed using the delayed fluorescent material.

Further, the light-emitting layer produced by using the indenocarbazole compound according to the present invention may have a structure that another light-emitting layer produced by using a compound having a different work function as the host material is laminated adjacent to the light-emitting layer.

<Hole Blocking Layer>

Any known compound having a hole blocking action can be used for the hole blocking layer 7. Examples of the known compound having a hole blocking action include a phenanthroline derivative such as bathocuproine (BCP); a metal complex of a quinolinol derivative such as aluminum (III)bis(2-methyl-8-quinolinato)-4-phenylphenolate (BAlq); a dibenzothiophene derivative such as 2,8-bis(diphenylphosphoryl)dibenzo[b, d]thiophene (PPT); a benzonitrile derivative; various rare earth complexes; an oxazole derivative; a triazole derivative; a triazine derivative; and the like. These materials may also serve as a material of the electron transporting layer.

<Electron Transporting Layer>

Any known electron transporting material can be used for the electron transporting layer 8. Examples of the known electron transporting material include various metal complexes including a metal complex of a quinolinol derivative such as $Alq_3$ and BAlq; a triazole derivative; a benzonitrile derivative; a triazine derivative; an oxadiazole derivative; a pyridine derivative; a pyrimidine derivative; a thiadiazole derivative; a benzotriazole derivative; a carbodiimide derivative; a quinoxaline derivative; a pyridoindole derivative; a phenanthroline derivative; a silole derivative; a compound having an anthracene ring structure; a benzimidazole derivatives such as TPBI; and the like.

Further, with respect to the material commonly used in the electron transporting layer, a material to which metal such as cesium or a triarylphosphine oxide derivative (WO 2014/195482) is N-doped can be used.

<Electron Injecting Layer>

On the electron transporting layer 8, an electron injecting layer 9 may be provided. As the electron injecting layer 9, an alkali metal salt such as cesium fluoride and lithium fluoride; an alkaline earth metal salt such as magnesium fluoride; a metal oxide such as aluminum oxide; and the like can be used. It is possible to omit the electron injecting layer 9 by preferably selecting the electron transporting layer and the cathode.

Further, with respect to the material commonly used in the electron transporting layer, a material to which metal such as cesium or a triarylphosphine oxide derivative (WO 2014/195482) is N-doped can be used.

<Cathode>

As the cathode 10, an electrode material having a low work function such as aluminum and an electrode material having a lower work function such as a magnesium-silver alloy, a magnesium-indium alloy, and an aluminum magnesium alloy are used.

EXAMPLES

Hereinafter, embodiments of the present invention will be specifically described by illustrative examples, but the present invention is not limited to the following examples.

Example 1: Compound 1

| Synthesis of 7-(12,12-dimethyl-indeno[2,1-b]carbazole-10-yl)-10-phenyl-12,12-dimethyl-indeno[2,1-b]carbazole | To a reaction vessel purged with nitrogen, |
|---|---|
| xylene | 100 mL, |
| 7-bromo-10-phenyl-12,12-dimethyl-indeno[2,1-b]carbazole | 5.0 g, |
| 7,7-dimethyl-indeno[2,1-b]carbazole | 3.6 g, |
| t-butoxy sodium | 1.6 g, |
| t-butylphosphine | 0.2 g, and |
| palladium acetate | 0.1 g | were added, heated, and stirred at 120° C. for 5 hours to give a reaction solution. The reaction solution was allowed to cool to room temperature, water was added, and the solution was extracted with toluene. A collected organic layer was concentrated to give a crude product. The crude product was purified by column chromatography (carrier: silica gel, eluent: toluene/hexane). As a result, a white solid of a compound 1 was provided (83% yield).

The resulting white solid was identified by using the NMR and the structure was identified. A ¹H-NMR chart is shown in FIG. 1. By the ¹H-NMR (CDCl$_3$), the following 36 signals of hydrogen were detected.

δ (ppm)=8.49 (1H)
8.44 (1H)
8.41 (1H)
8.24 (1H)
7.88 (1H)
7.81 (1H)
7.78-7.67 (4H)
7.64-7.52 (3H)
7.49-7.23 (11H)
1.54 (6H)
1.49 (6H).

[Chemical formula 7]

(Compound 1)

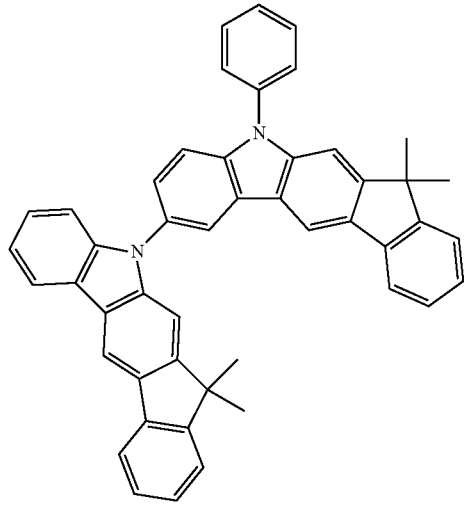

Example 2: Compound 2

| Synthesis of 7-(carbazol-9-yl)-10-phenyl-12,12-dimethyl-indeno[2,1-b]carbazole | To a reaction vessel purged with nitrogen, |
|---|---|
| xylene | 100 mL, |
| 7-bromo-10-phenyl-12,12-dimethyl-indeno[2,1-b]carbazole | 6.0 g, |
| carbazole | 2.5 g, |
| t-butoxy sodium | 2.0 g, |
| t-butylphosphine | 0.2 g, and |
| palladium acetate | 0.1 g | were added, heated, and stirred at 120° C. for 5 hours to give a reaction solution. The reaction solution was allowed to cool to room temperature, water was added, and the solution was extracted with toluene. A collected organic layer was concentrated to give a crude product. The crude product was purified by the column chromatography (carrier: silica gel, eluent: toluene/hexane). As a result, a white solid of a compound 2 was provided (60% yield).

Figure 2:
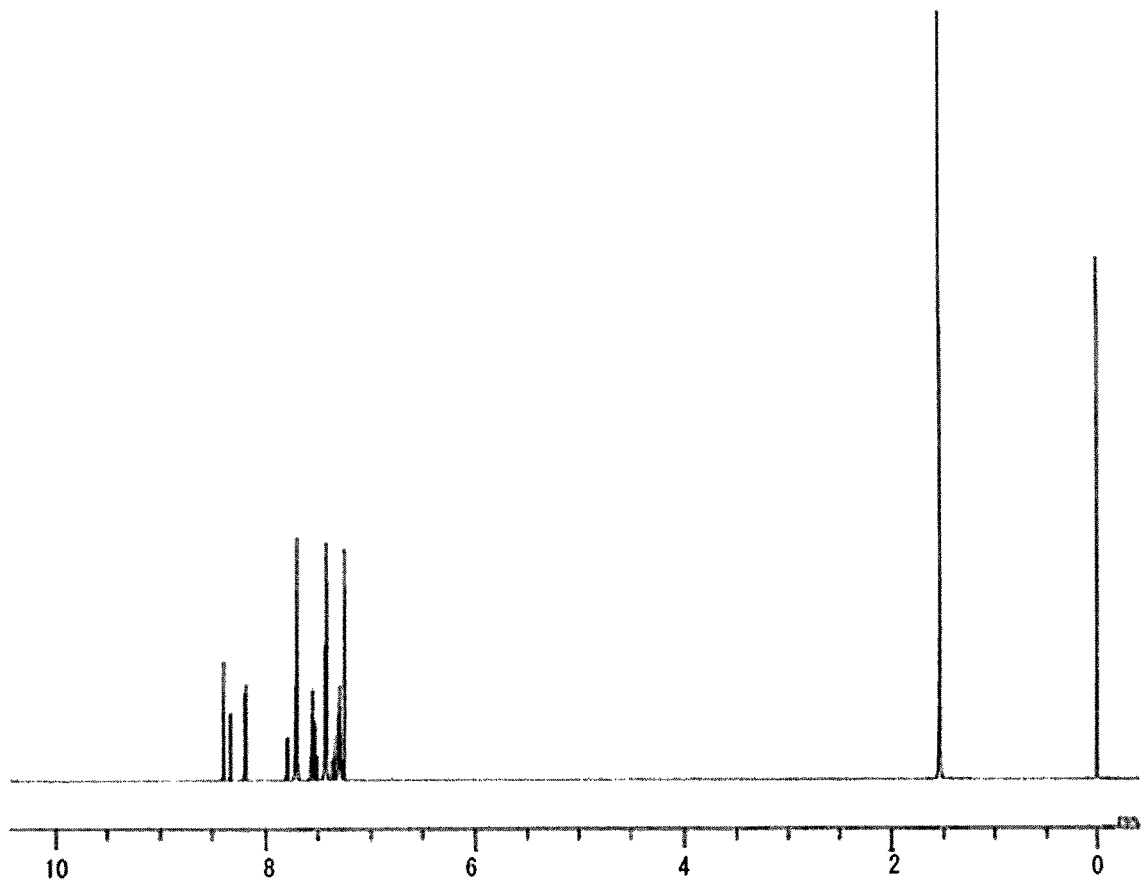
FIG. 2 is a $^1$H-NMR chart diagram of Compound 2 in Example 2.

The resulting white solid was identified by using the NMR and the structure was identified. A ¹H-NMR chart is shown in FIG. 2. By the ¹H-NMR (CDCl$_3$), the following 28 signals of hydrogen were detected.

δ (ppm)=8.41 (1H)
8.34 (1H)
8.19 (2H)
7.80 (1H)
7.75-7.68 (4H)
7.62-7.50 (3H)
7.48-7.39 (6H)
7.39-7.25 (4H)
1.53 (6H)

[Chemical formula 8]

(Compound 2)

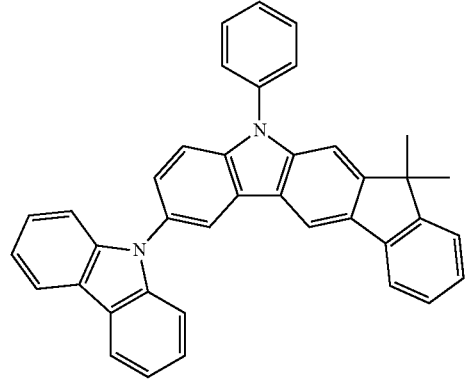

Example 3: Compound 3

| Synthesis of 7-(carbazol-9-yl)-10-(biphenyl-4-yl)-12,12-dimethyl-indeno[2,1-b]carbazole | To a reaction vessel purged with nitrogen, |
|---|---|
| toluene | 50 mL, |
| 7-Bromo-10-(biphenyl-4-yl) 12,12-dimethyl-indeno[2,1-b] carbazole | 3.0 g, |
| carbazole | 1.1 g, |
| t-butoxy sodium | 0.7 g, |

-continued

| | |
|---|---|
| t-butylphosphine | 0.1 g, and |
| palladium acetate | 0.1 g | were added, heated, and stirred at 110° C. for 5 hours to give a reaction solution. The reaction solution was allowed to cool to room temperature, water was added, and the solution was extracted with toluene. A collected organic layer was concentrated to give a crude product. The crude product was purified by the column chromatography (carrier: silica gel, eluent: toluene/hexane). As a result, a white solid of a compound 3 was provided (56% yield).

Figure 3:
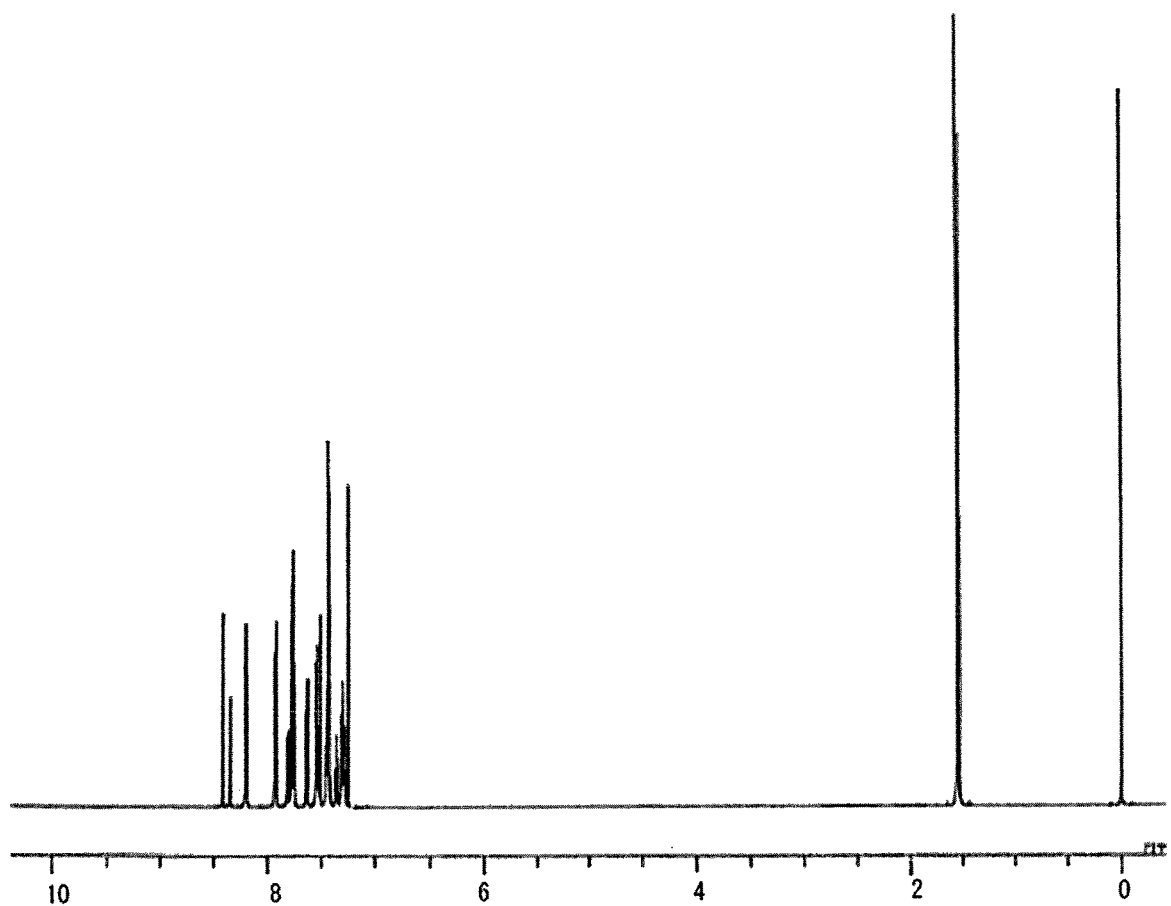
FIG. 3 is a $^1$H-NMR chart diagram of Compound 3 in Example 3.

The resulting white solid was identified by using the NMR and the structure was identified. A $^1$H-NMR chart is shown in FIG. 3. By the $^1$H-NMR (CDCl$_3$), the following 32 signals of hydrogen were detected.

δ (ppm)=8.42 (1H)
8.35 (1H)
8.20 (2H)
7.96-7.88 (2H)
7.84-7.73 (5H)
7.63 (1H)
7.59-7.48 (4H)
7.48-7.26 (10H)
1.55 (6H)

[Chemical formula 9]

(Compound 3)

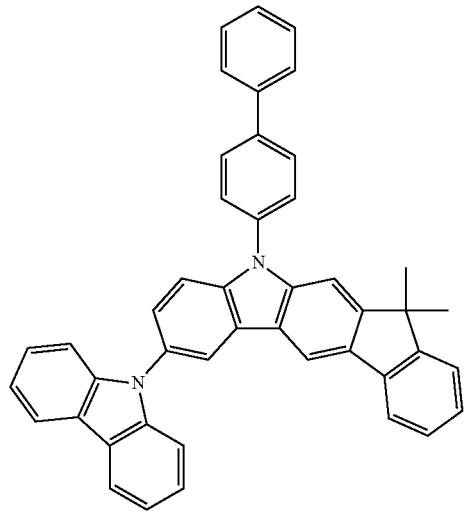

Example 4: Compound 24

| Synthesis of 7,10-bis(2-dibenzofuranyl)-10H,12H-12,12-dimethyl-indeno[2,1-b]carbazole; | To a reaction vessel purged with nitrogen, |
|---|---|
| xylene | 70 mL, |
| 2-bromo-dibenzofuran | 1.8 g, |
| 7-(2-dibenzofuranyl)-10H,12H-12,12-dimethyl-indeno [2,1-b] carbazole | 3.0 g, |
| t-butoxy sodium | 1.0 g, |
| t-butylphosphine | 0.1 g, and |
| palladium acetate | 0.3 g | were added, heated, and stirred at 130° C. for 11 hours to give a reaction solution. The reaction solution was allowed to cool to room temperature, water was added, and the solution was extracted with toluene. A collected organic layer was concentrated to give a crude product. The crude product was purified by the column chromatography (carrier: silica gel, eluent: toluene/hexane). As a result, a white solid of a compound 24 was provided (30% yield).

Figure 4:
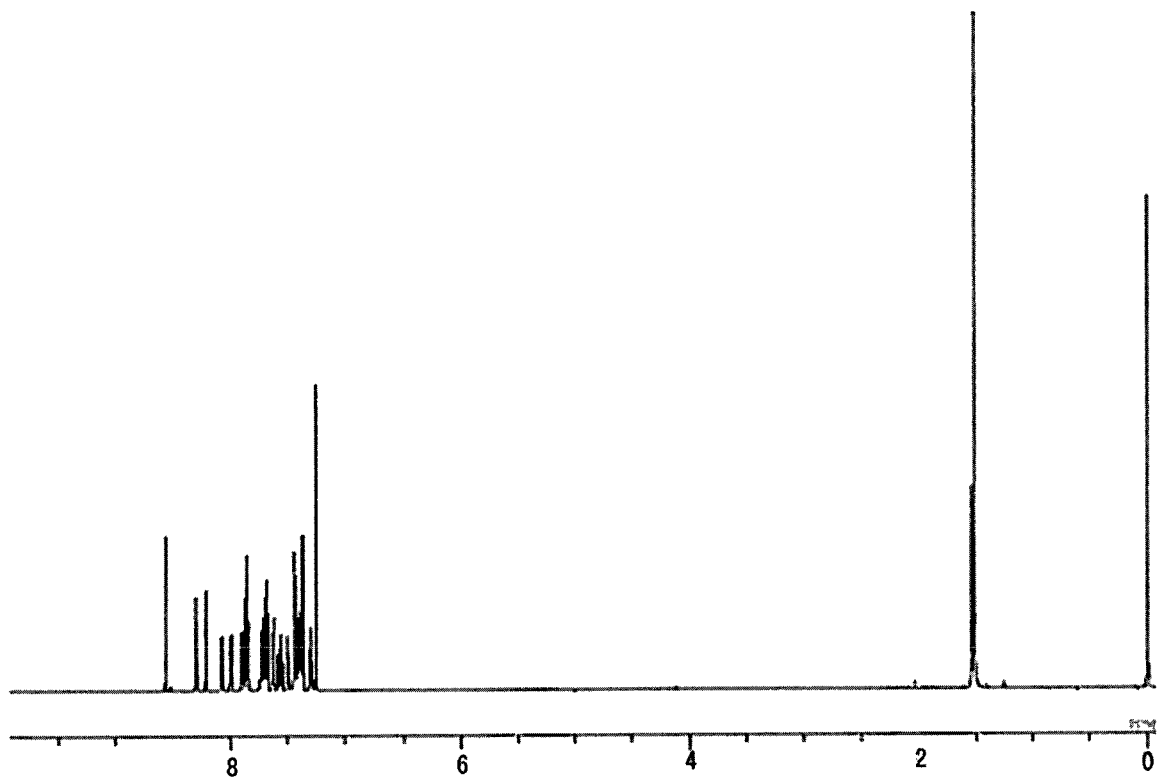
FIG. 4 is a $^1$H-NMR chart diagram of Compound 24 in Example 4.

The resulting white solid was identified by using the NMR and the structure was identified. A $^1$H-NMR chart is shown in FIG. 4. By the $^1$H-NMR (CDCl$_3$), the following 29 signals of hydrogen were detected.

δ (ppm)=8.56 (1H)
8.51 (1H)
8.30 (1H)
8.29 (1H)
8.20 (1H)
8.06 (1H)
8.00-7.84 (3H)
7.73-7.67 (4H)
7.61 (1H)
7.56 (1H)
7.49 (1H)
7.44-7.39 (6H)
7.29 (1H)
1.52 (6H)

[Chemical formula 10]

(Compound 24)

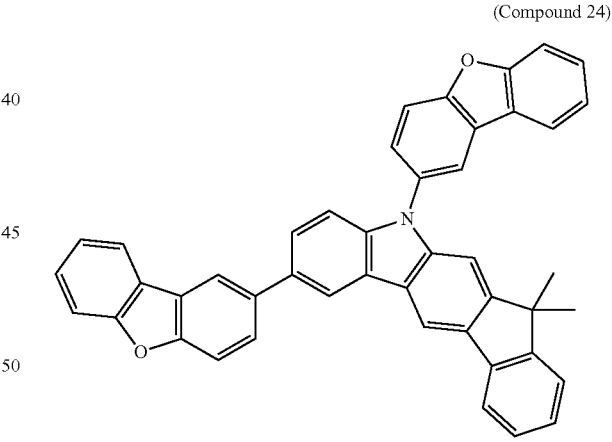

The high sensitivity differential scanning calorimeter (manufactured by Bruker AXS, DSC3100S) was used to determine the glass transition point of the compound obtained in each example.

| | Glass transition point (° C.) |
|---|---|
| Compound 1 of Example 1 | 189.3 |
| Compound 2 of Example 2 | 143.2 |
| Compound 3 of Example 3 | 160.1 |
| Compound 24 of Example 4 | 147.7 |

It was found that each of the indenocarbazole compounds according to the present invention had the glass transition temperature of 100° C. or more and had a stable thin film state.

Using the compound obtained in each example, a deposited film having a thickness of 100 nm was formed on an ITO substrate and was measured for the work function using the ionization potential measuring apparatus (manufactured by Sumitomo Heavy Industries, Ltd., PYS-202 type).

|  | Work function (eV) |
|---|---|
| Compound 1 of Example 1 | 5.79 |
| Compound 2 of Example 2 | 5.94 |
| Compound 3 of Example 3 | 5.86 |
| Compound 24 of Example 4 | 5.81 |

It was found that each of the indenocarbazole compounds according to the present invention showed a preferable energy level and had good hole transportability as compared to the work function 5.5 eV of general hole transporting material such as NPD and TPD.

Device Example 1

As shown in FIG. 5, on the glass substrate 1 on which an ITO electrode was formed in advance as the transparent anode 2, the hole injecting layer 3, the hole transporting layer 4, the electron blocking layer 5, the light-emitting layer 6, the hole blocking layer 7, the electron transporting layer 8, the electron injecting layer 9, and the cathode (aluminum electrode) 10 were vapor-deposited in this order to produce an organic EL device that emits the delayed fluorescence.

Specifically, after the glass substrate 1 on which ITO having a thickness of 150 nm was formed was washed with an organic solvent, the surface was cleaned by UV ozone treatment. After that, the glass substrate including the ITO electrode was mounted in a vacuum deposition apparatus, of which pressure was reduced to 0.001 Pa or less.

Subsequently, a compound HIM-1 having the following formula was vapor-deposited so as to cover the transparent anode 2 to form the hole injecting layer 3 having a thickness of 10 nm.

[Chemical formula 11]

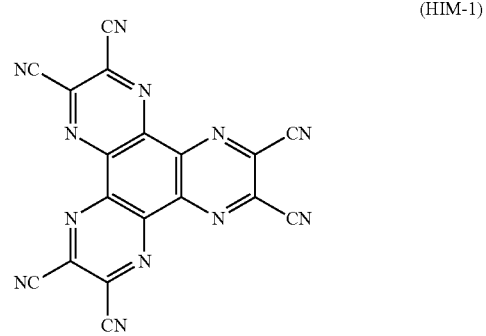

(HIM-1)

On the hole injecting layer 3, HTM-1 represented by the following structural formula was vapor-deposited to form the hole transporting layer 4 having a film thickness of 25 nm.

[Chemical formula 12]

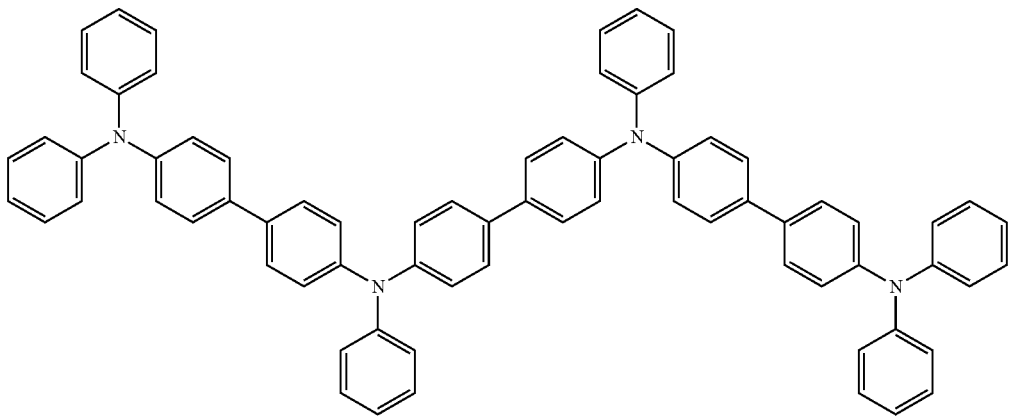

(HTM-1)

On the hole transporting layer 4, the compound 1 of Example 1 was vapor-deposited to form the electron blocking layer 5 having a thickness of 5 nm.

[Chemical formula 13]

(Compound 1)

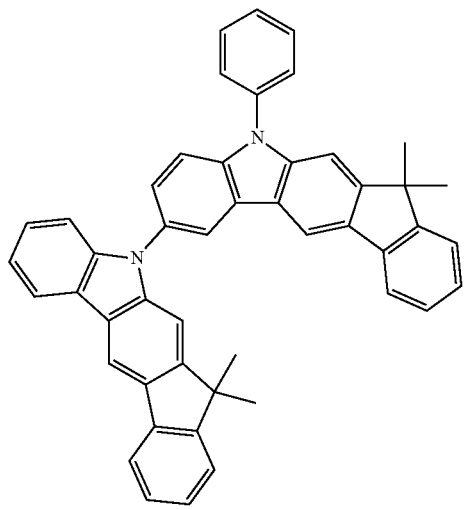

On the electron blocking layer 5, EMD-1 (4CzIPN) represented by the following structural formula as the dopant material and EMH-1 (mCBP) expressed by the following structural formula as the host material were binary vapor-deposited at a vapor-deposition rate such that a ratio of a vapor-deposition rates was EMD-1:EMH-1=15:85 to form the light-emitting layer 6 having a thickness of 30 nm.

Note that the EMD-1 is a heat activated delayed fluorescent material.

[Chemical formula 14]

(EMD-1)

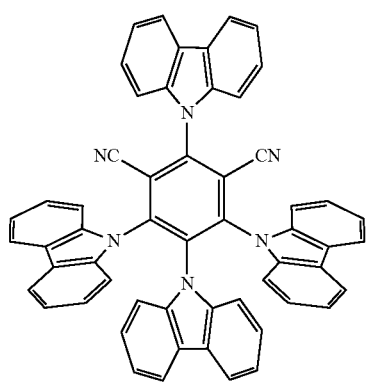

(EMH-1)

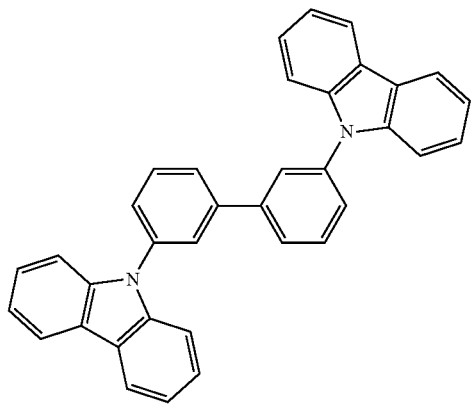

On the light-emitting layer 6, ETM-1 represented by the following structural formula was vapor-deposited to form the hole blocking layer 7 having a thickness of 10 nm.

[Chemical formula 15]

(ETM-1)

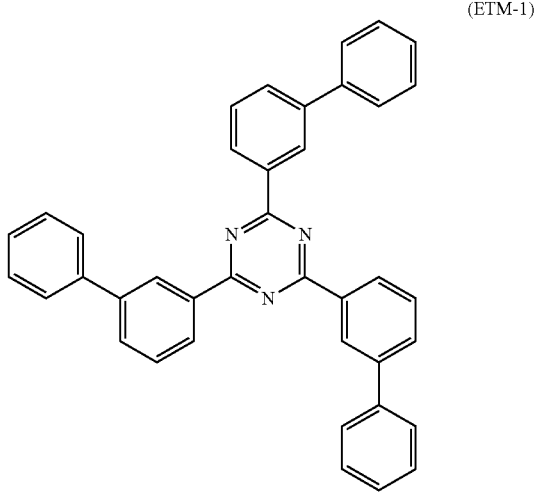

On the hole blocking layer 7, ETM-2 represented by the following structural formula was vapor-deposited to form the electron transporting layer 8 having a thickness of 40 nm.

[Chemical formula 16]

(ETM-2)

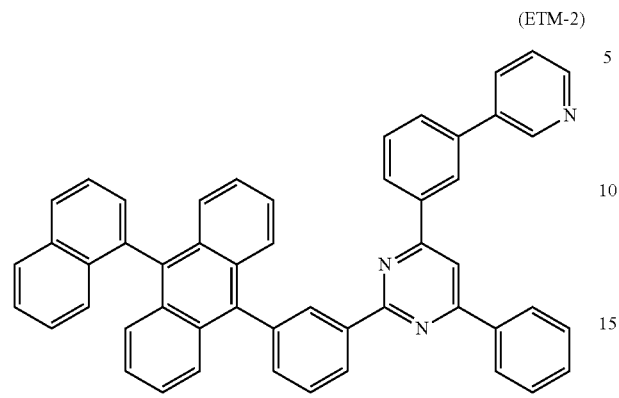

On the electron transporting layer 8, lithium fluoride was vapor-deposited to form the electron injecting layer 9 having a thickness of 1 nm.

Finally, aluminum was vapor-deposited on the electron injecting layer 9 to form the cathode 10 having a film thickness of 100 nm.

Device Example 2

An organic EL device that emits the delayed fluorescence at the same conditions was produced except that the electron blocking layer 5 was formed by using the compound 2 of Example 2 in place of the compound 1 of Example 1 in Device Example 1.

[Chemical formula 17]

(Compound 2)

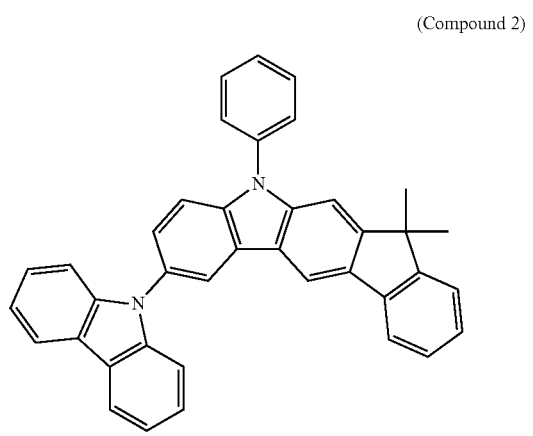

Device Example 3

An organic EL device that emits the delayed fluorescence at the same conditions was produced except that the electron blocking layer 5 was formed by using the compound 3 of Example 3 in place of the compound 1 of Example 1 in Device Example 1.

[Chemical formula 18]

(Compound 3)

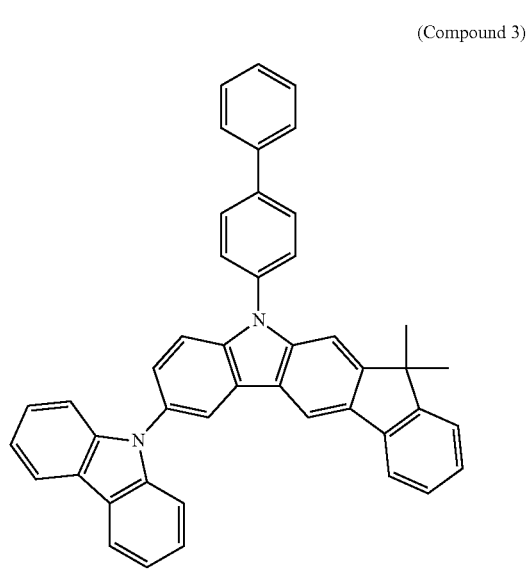

Device Example 4

An organic EL device that emits the delayed fluorescence at the same conditions was produced except that the electron blocking layer 5 was formed by using the compound 24 of Example 4 in place of the compound 1 of Example 1 in Device Example 1.

[Chemical formula 19]

(Compound 24)

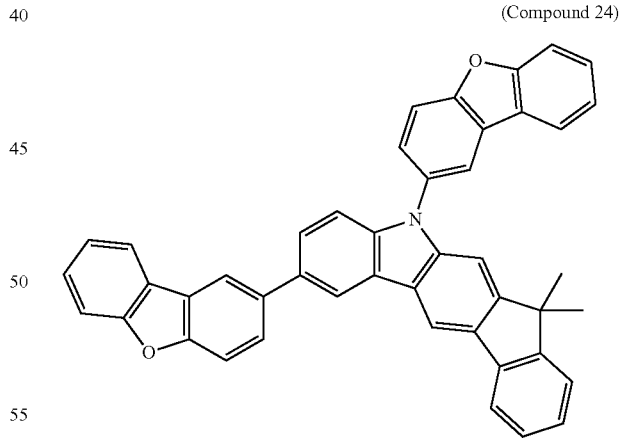

Comparative Device Example 1

An organic EL device that emits the delayed fluorescence at the same conditions was produced except that the electron blocking layer 5 was formed by using HTM-A of the following structural formula in place of the compound 1 of Example 1 in Device Example 1.

[Chemical formula 20]

(HTM-A)

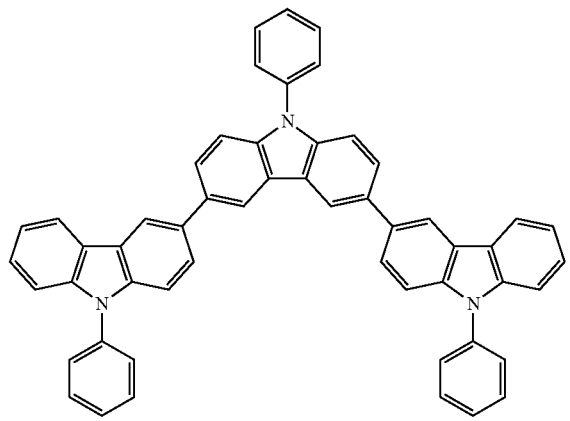

The organic EL devices produced in Device Examples 1 to 4 and Comparative Device Example 1 were measured for properties in the atmosphere at room temperature. Table 1 shows measurement results of light-emitting properties when a direct voltage is applied to each of the organic EL devices produced.

The device lifetimes were measured by using organic EL devices produced in Device Examples 1 to 4 and Comparative Device Example 1. Specifically, when each device was driven with a constant current at light-emitting brightness (initial brightness) of 1000 cd/m$^2$ at the start of emitting light, the time to decay the light-emitting brightness to 950 cd/m$^2$ (corresponding to 95% of the initial brightness taking as 100%: 95% decay) was measured. Table 1 shows the results.

TABLE 1

| | Electron blocking layer | Brightness [cd/m$^2$] (@10 mA/cm$^2$) | Light-emitting efficiency [cd/A] (@10 mA/cm$^2$) | Power efficiency [lm/W] (@10 mA/cm$^2$) | Device lifetime [h] 95% decay |
|---|---|---|---|---|---|
| Device Example 1 | Compound 1 | 4662 | 46.7 | 25.5 | 240 |
| Device Example 2 | Compound 2 | 5325 | 53.3 | 27.0 | 151 |
| Device Example 3 | Compound 3 | 5093 | 51.0 | 27.3 | 125 |
| Device Example 4 | Compound 24 | 5375 | 53.8 | 29.6 | 109 |
| Device Comparative Example 1 | HTM-A | 4653 | 46.6 | 27.0 | 151 |

When a current of 10 mA/cm$^2$ flowed, while the brightness of Comparative Device Example 1 was 4653 cd/m$^2$, the brightness of any of Device Examples 1 to 4 was high, i.e., 4662 to 5375 cd/m$^2$.

While the light-emitting efficiency of Comparative Device Example 1 was 46.6 cd/A, the light-emitting efficiencies of Device Examples 1 to 4 were high, i.e., 46.7 to 53.8 cd/A.

While the power efficiency of Comparative Device Example 1 was 27.0 lm/W, the power efficiencies of Device Examples 2 to 4 were similar thereto or more, i.e., 27.0 to 29.6 lm/W.

While the device lifetime (95% decay) of Comparative Device Example 1 was 151 hours, the device lifetime of Device Example 1 was 240 hours and had a significantly longer lifetime.

Note that as to the voltage at the time of current density of 10 mA/cm$^2$, it was confirmed that Device Examples 1 to 4 and Comparative Device Example 1 had the similar voltage.

From the above results, it was found that the organic EL device using the indenocarbazole compound according to the present invention for the electron blocking layer and the heat activated delayed fluorescent material as the dopant material of the light-emitting layer had a high light-emitting efficiency and high brightness as compared with the known organic EL device using the HTM-A, and that a high power efficiency or a long lifetime can be achieved depending on the structure of the indenocarbazole compound.

Further, Device Examples 1 and 2 having the electron blocking layers 5 formed by using the indenocarbazole compounds having the same structure other than X in the formula (1) were compared. As a result, Device Example 1 using the compound 1 had the lifetime much longer than Device Example 2 using the compound 2, since the compound 1 had X being the indenocarbazolyl group, i.e., two indenocarbazole structures in the molecule and the compound 2 had X being the carbazolyl group.

Similarly, Device Examples 2 and 3 having the electron blocking layers 5 formed by using the indenocarbazole compounds having the same structure other than R$^1$ in the formula (1) were compared. As a result, Device Example 2 using the compound 2 had the lifetime much longer than Device Example 3 using the compound 3, since the compound 2 had R$^1$ that was the phenyl group being the aromatic hydrocarbon group having one aromatic ring and the compound 3 had R$^1$ that was the biphenyl group being the aromatic hydrocarbon group having two or more aromatic rings.

Furthermore, Device Examples 1 to 3 and Device Example 4 having the electron blocking layers 5 formed by using the indenocarbazole compounds that were different in that X and R$^1$ in the formula (1) were the oxygen-containing aromatic heterocyclic group or not. As a result, Device Examples 1 to 3 using the compounds 1 to 3 having X and R$^1$ not being the oxygen-containing aromatic heterocyclic group had the lifetime longer than Device Example 4 using the compound 24 having X and R$^1$ being the oxygen-containing aromatic heterocyclic groups. On the other hand, Device Example 4 had the brightness, the light-emitting efficiency, and the power efficiency better than Device Examples 1-3.

INDUSTRIAL APPLICABILITY

As described above, the indenocarbazole compound according to the present invention has the hole transporting properties and is excellent in the electron blocking properties, and a thin film state is stable. Thus, the indenocarbazole compound according to the present invention is the excellent compound for the organic EL device. The organic EL device according to the present invention produced using the compound has a high light-emitting efficiency and high brightness. Accordingly, the organic EL device according to the present invention can be applied to household electric appliances and lighting applications.

REFERENCE SIGNS LIST 1 glass substrate
2 transparent anode
3 hole injecting layer
4 hole transporting layer
5 electron blocking layer
6 light-emitting layer
7 hole blocking layer
8 electron transporting layer
9 electron injecting layer
10 cathode

The invention claimed is:

1. An organic electroluminescence device having a pair of electrodes and at least one organic layer sandwiched therebetween,
wherein an indenocarbazole compound is adapted to be used as a constituent material of at least one organic layer,
wherein the indenocarbazole compound has hole transporting properties and is represented by the following general Chemical formula (1)

[Chemical formula 1]

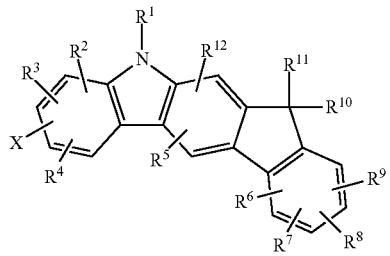

(1)

wherein $R^1$ represents an unsubstituted phenyl group, an unsubstituted diphenyl group, or an unsubstituted dibenzofuranyl group;
wherein $R^2$ to $R^{12}$ may be the same or different and each represents a hydrogen atom, a deuterium atom, a fluorine atom, a chlorine atom, a cyano group, a nitro group, an alkyl group having 1 to 8 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or disubstituted amino group substituted with an aromatic hydrocarbon group or an aromatic heterocyclic group; $R^1$ to $R^{12}$ may bond to form a ring via a single bond, a substituted or unsubstituted methylene group, an oxygen atom, or a sulfur atom; and wherein $R^{10}$ and $R^{11}$ are not bonded to each other via a single bond, a substituted or unsubstituted methylene group, an oxygen atom, or a sulfur atom; and
wherein X represents an unsubstituted carbazolyl group or an unsubstituted dibenzofuranyl group.

2. The organic electroluminescence device according to claim 1, wherein the organic layer is a hole transporting layer, an electron blocking layer, a hole injecting layer, or a light-emitting layer.

3. The organic electroluminescence device according to claim 1, wherein the organic electroluminescence device is adapted to emit delayed fluorescence.

4. An organic electroluminescence device, having a light-emitting layer between a pair of electrodes,
wherein an indenocarbazole compound is adapted to be used as a constituent material of the light-emitting layer,
wherein the indenocarbazole compound has hole transporting properties and is represented by the following general Chemical formula (1)

[Chemical formula 1]

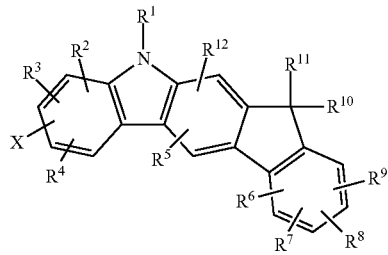

(1)

wherein $R^1$ represents an unsubstituted phenyl group, an unsubstituted diphenyl group, or an unsubstituted dibenzofuranyl group;
wherein $R^2$ to $R^{12}$ may be the same or different and each represents a hydrogen atom, a deuterium atom, a fluorine atom, a chlorine atom, a cyano group, a nitro group, an alkyl group having 1 to 8 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbongroup, an aromatic heterocyclic group, an aryloxy group, or disubstituted amino group substituted with an aromatic hydrocarbon group or an aromatic heterocyclic group; $R^1$ to $R^{12}$ may bond to form a ring via a single bond, a substituted or unsubstituted methylene group, an oxygen atom, or a sulfur atom; and wherein $R^{10}$ and $R^{11}$ are not bonded to each other via a single bond, a substituted or unsubstituted methylene group, an oxygen atom, or a sulfur atom; and
wherein X represents an unsubstituted carbazolyl group or an unsubstituted dibenzofuranyl group.

5. The organic electroluminescence device according to claim 4, wherein the organic electroluminescence device is adapted to emit delayed fluorescence.

6. An organic electroluminescence device having a light-emitting layer and other layer between a pair of electrodes,
   wherein the other layer is a hole injecting layer, a hole transporting layer, or an electron blocking layer,
   wherein an indenocarbazole compound is adapted to be used as a constituent material of the light-emitting layer or the other layer,
   wherein the indenocarbazole compound has hole transporting properties and is represented by the following general Chemical formula (1)

[Chemical formula 1]

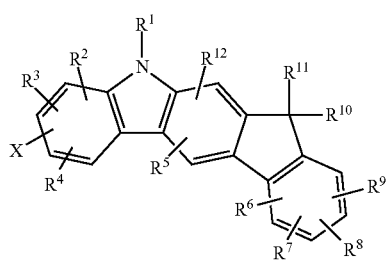

(1)

wherein $R^1$ represents an unsubstituted phenyl group, an unsubstituted diphenyl group, or an unsubstituted dibenzofuranyl group;

wherein $R^2$ to $R^{12}$ may be the same or different and each represents a hydrogen atom, a deuterium atom, a fluorine atom, a chlorine atom, a cyano group, a nitro group, an alkyl group having 1 to 8 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, an aryloxy group, or disubstituted amino group substituted with an aromatic hydrocarbon group or an aromatic heterocyclic group; $R^1$ to $R^{12}$ may bond to form a ring via a single bond, a substituted or unsubstituted methylene group, an oxygen atom, or a sulfur atom; and wherein $R^{10}$ and $R^{11}$ are not bonded to each other via a single bond, a substituted or unsubstituted methylene group, an oxygen atom, or a sulfur atom; and wherein X represents an unsubstituted carbazolyl group or an unsubstituted dibenzofuranyl group.

7. The organic electroluminescence device according to claim 6, wherein the organic electroluminescence device is adapted to emit delayed fluorescence.

* * * * *